United States Patent [19]

Oshida et al.

[11] Patent Number: 5,972,943
[45] Date of Patent: Oct. 26, 1999

[54] PYRIDINECARBOXAMIDE DERIVATIVES

[75] Inventors: Norio Oshida; Yoji Mimaki; Hiroaki Satoh, all of Ohimachi; Shinji Yokoyama, Komoro; Yukiko Muraki, Ohimachi; Kazumi Nishimura, Ohimachi; Tamiko Hamada, Ohimachi; Einosuke Sakurai, Ohimachi; Hiroshi Sakai, Ohimachi; Toshiji Sugai, Ohimachi; Tomomi Tonoike, Ohimachi; Koichi Itoh, Ohimachi, all of Japan

[73] Assignee: Nisshin Flour Milling Co., Ltd., Tokyo, Japan

[21] Appl. No.: 09/101,760

[22] PCT Filed: Nov. 19, 1997

[86] PCT No.: PCT/JP97/04207

§ 371 Date: Jul. 20, 1998

§ 102(e) Date: Jul. 20, 1998

[87] PCT Pub. No.: WO98/22439

PCT Pub. Date: May 28, 1998

[30] Foreign Application Priority Data

Nov. 19, 1996 [JP] Japan ................................. 8-308509

[51] Int. Cl.⁶ ........................ A61K 31/495; C07D 401/04
[52] U.S. Cl. ........................................... 514/252; 544/365
[58] Field of Search ............................. 544/365; 514/252

[56] References Cited

U.S. PATENT DOCUMENTS

| | | | |
|---|---|---|---|
| 4,994,456 | 2/1991 | Miura et al. | 514/218 |
| 5,025,012 | 6/1991 | Miura et al. | 514/252 |
| 5,250,526 | 10/1993 | Miura et al. | 514/218 |

FOREIGN PATENT DOCUMENTS

| | | |
|---|---|---|
| 3-7258 | 1/1991 | Japan . |
| 3-137095 | 6/1991 | Japan . |
| 5-32630 | 2/1993 | Japan . |

OTHER PUBLICATIONS

Stroke, A Journal of Cerebral Circulation, Nov.–Dec. 1981, vol. 12, No. 6 Thresholds in Cerebral Ischemia—The Ischemic Penumbra.

Kenji Inamura et al., Brain Nerve, 44(9): 779–785, 1992.

Takao Asano, et al., Neurosurgery, 13(11): 1147–1159, 1985.

Takaaki Kirino, Brain Research, 239: 57–69, 1982.

A. Ogura, et al., Exp. Brain Res. 73:447–458, 1988.

E. Sakurai et al., JPN. J. Pharmacol., vol. 61, No. Suppl. 1, p. 421, p. 289, 1993.

D.R. Lisk et al., Hypertention, Arch Neurol, 50: 855–862, 1993.

H. Nishi et al., Stroke, 20: 1236–1240, 1989.

*Primary Examiner*—Mukund J. Shah
*Assistant Examiner*—Ann M. Kessinger
*Attorney, Agent, or Firm*—Oblon, Spivak, McClelland, Maier & Neustadt, P.C.

[57] ABSTRACT

Pyridinecarboxamide derivatives of the formula

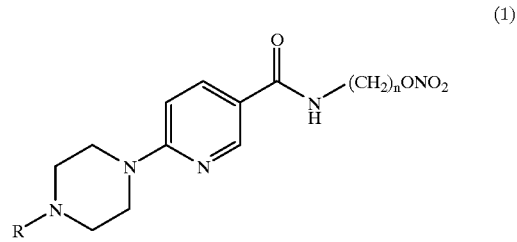

(1)

(wherein n represents an integer of 14–18, and R represents a hydrogen atom or a straight or branched $C_1$–$C_4$ alkyl group) or physiologically acceptable salts thereof. The compounds have excellent inhibiting activity of cerebral edema, especially ischemic cerebral edema, and inhibiting activity of delayed death of neuronal cells (an inhibiting activity of Ca-influx in neuronal cells). Cerebral edema is a pathologic condition accompanying cerebrovascular disorders, especially the acute stage of cerebrovascular disorders and then the compounds are useful as an agent for inhibiting cerebral edema or a therapeutic agent for cerebrovascular disorders. Moreover, the compounds have no hypotensive action which is considered to be side-effect in treating the acute stage cerebrovascular disorders and hardly show a behavior suppressing action so that they are an excellent therapeutic agent for, in particular, the acute stage cerebrovascular disorders. Moreover, the compounds show a cerebral protective activity (an anti-anoxic activity), an increasing activity of cerebral blood flow, and an inhibiting activity of lipid peroxidation and these activities may lead to the increased utility as a therapeutic agent for cerebrovascular disorders.

11 Claims, No Drawings

PYRIDINECARBOXAMIDE DERIVATIVES

TECHNICAL FIELD

This invention relates to a novel pyridinecarboxamide derivative. More particularly, this invention relates to an N-(ω-nitroxyalkyl)-6-piperazinylpyridine-3-carboxamide derivative, a process for the preparation thereof and a pharmaceutical preparation which comprises as an active ingredient said derivative. Moreover, this invention relates to a therapeutic agent for cerebrovascular disorders or cerebral edema which comprises as an active ingredient said pyridinecarboxamide derivative. Moreover, this invention relates to a method for the treatment of cerebrovascular disorders or cerebral edema which comprises administering said pyridinecarboxamide derivative. Moreover, this invention relates to an intermediate for the synthesis of said pyridinecarboxamide derivative.

BACKGROUND ART

Neuronal cells are weak to ischemia and may easily be damaged, but there is a recoverable area around the ischemic neuronal cells, which is referred to as the "Penumbra" (Astrup, J., Siesjo, B., Symon, L.; Stroke, 12:723–725 1981). In the therapy of cerebrovascular disorders at the acute stage, it is important to protect the neuronal cells in the penumbra area from cell damage and maintain cerebral functions.

It has been known that cerebrovascular disorders caused by ischemia may accompany cerebral edema with an unusually increased moisture content in the brain in the ischemic center and penumbra area (Kenji Inamura and Akiro Terashi: Brain Nerv. 44(9):779–785, 1992). Cerebral edema may be also caused by cerebral tumor, encephalitis, heat stroke, cerebral trauma by a traffic accident. The edema may increase the cerebral capacity, which results in the increase in cerebral pressure, because the brain is closed within the hard skull. A precipitous increase in cerebral pressure may cause cerebral hernia, which makes patients fall in the dangerous state of their life.

Cerebral edema may accompany sodium and calcium influx into neuronal cells, which are found at a higher concentration extracellularly as compared with the intracellular one (Takao Asano, Hiroo Johshita, Osamu Gotoh and others: Cerebral Surgery 13:1147–1159, 1985), and it is believed that calcium influx may activate calcium-dependent enzymes (proteases, phospholipases or the like), which results in the damage of cytoskeleton or cell membrane.

Activation of phospholipase A2, a phospholipase, may release arachidonic acid from the phospholipid in cell membrane. Accumulation of the arachidonic acid may inhibit respiration of mitochondria to decrease ATP. Moreover, it is believed that peroxidation of lipids by the free radicals produced during the metabolism of arachidonic acid may cause disorders of cell membrane or increased permeability of the membrane to provoke the progress of the edema.

In addition to such acute disorders of neuronal cells, the phenomenon referred to as the delayed neuronal death has been found out (Kirino T., Brain Res., 239:57–69, 1982). This means the phenomenon that the neuronal cells after a short period of ischemia fall off after several days to several weeks. It has now been elucidated that delayed cellular death such as delayed neuronal death is related with a calcium concentration in neuronal cells (Ogura, A., Miyamoto, M., Kudo, Y., Exptl. Brain Res., 73:447–458, 1988). Such being the case, it is the important object in the treatment of cerebrovascular disorders at the acute stage to inhibit cerebral edema which would greatly influence upon the prognosis for life of patients and also could be the cause of acute and delayed neuronal death.

Presently there has been mainly applied an osmotherapy for the treatment of cerebral edema. In this method, a liquid of hyperosmorality is injected into blood, whereby an osmotic pressure in blood is raised and moisture is withdrawn from edema tissues. However, satisfactory effects have not been attained as yet and there has been desired a novel anti-cerebral edema agent other than the osmotherapy.

On the other hand, our copending JP-A-5-32630 discloses that pyridinecarboxamide derivatives having a methylene chain of 9–13 carbon atoms and bonded to the amido nitrogen have an activity of increasing cerebral blood flow. Moreover, it was reported by Sakurai et al. that the compound of Example 10 of said JP-A-5-32630, namely, N-(11-nitroxy-1-undecanyl)-6-(4-methyl-1-piperazinyl) nicotinamide could show a cerebral protective effect on the hypoxia and anoxia models (Sakurai Einosuke, Jpn. J. Pharmacol., Vol. 61, No. suppl. 1 , PAGE 289p 1993).

However, it has also been elucidated that the compound disclosed in JP-A-5-32630 has a hypotensive activity though it has an activity of increasing cerebral blood flow. It has been elucidated that use of a potent hypotensive drug at the acute stage of cerebrovascular disorders causes ischemia in the penumbra area with a risk of extending lesions (Lisk, DR. et al.: Hypertension 50:855–862, 1993).

Accordingly, the agent for increasing cerebral blood flow as disclosed in JP-A-5-32630 is useful for treating cerebrovascular disorders at the chronic stage, but not suitable at the acute stage.

As the compounds having a cerebral protective action (an anti-anoxia action) would be expected to show an inhibiting action on cerebral edema, it has been attempted to review and pick up those compounds having an anti-anoxia action. However, the compounds disclosed in Example 10 of JP-A-5-32630 have been regarded as undesirable for the therapy of cerebrovascular disorders at the acute stage, because they were observed to possess a behavior suppressing activity that Nizofenone and others possess as a side-effect.

DISCLOSURE OF INVENTION

This invention relates to a pyridinecarboxamide derivative represented by the formula (1)

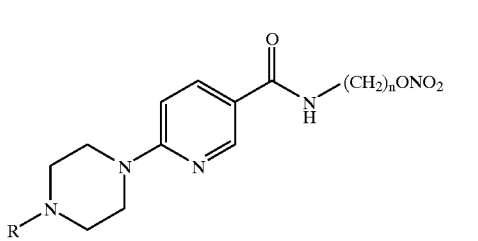

(1)

(wherein n represents an integer of 14–18 and R represents a hydrogen atom or a $C_1$–$C_4$ straight or branched alkyl group) or a physiologically acceptable salt thereof.

Moreover, this invention relates to a compound represented by the formula (2)

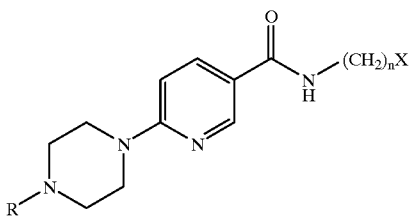

(2)

(wherein n and R are as defined above and X represents a hydroxy group, a mesyloxy group, a tosyloxy group, a bromine atom or an iodine atom).

Moreover, this invention relates to a 6-piperazinylpyridine-3-carboxylic acid represented by the formula (3)

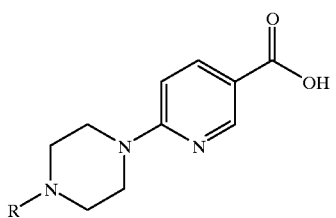

(3)

(wherein R is as defined above) or a metal salt or acid addition salt thereof.

Moreover, this invention relates to a process for the production of the pyridinecarboxamide derivative represented by the formula (1) which comprises reacting the compound represented by the formula (2) with a nitrating agent.

Moreover, this invention relates to a process for the production of the pyridinecarboxamide derivative represented by the formula (1) which comprises reacting an alkali metal salt, a halide or an anhydride of the 6-piperazinylpyridine-3-carboxylic acid represented by the formula (3) with an ω-aminoalkyl nitrate represented by the formula (4) —$H_2N(CH_2)_nONO_2$ (wherein n is as defined above) or an acid addition salt thereof.

Moreover, this invention relates to a pharmaceutical composition which comprises the pyridinecarboxamide derivative represented by the formula (1) or a physiologically acceptable salt thereof and a pharmaceutically acceptable excipient.

Moreover, this invention relates to a therapeutic agent for cerebrovascular disorders, especially cerebrovascular disorders at the acute stage, which comprises the pyridinecarboxamide derivative represented by the formula (1) or a physiologically acceptable salt thereof and a pharmaceutically acceptable excipient.

Moreover, this invention relates to a therapeutic agent for cerebrovascular disorders at the acute stage which is used for treating cerebrovascular disorders caused by cerebral infarction or subarachnoid hemorrhage.

Moreover, this invention relates to a therapeutic agent for cerebral edema which comprises the pyridinecarboxamide derivative represented by the formula (1) or a physiologically acceptable salt thereof and a pharmaceutically acceptable excipient.

Moreover, this invention relates to a method for the treatment of cerebrovascular disorders, especially cerebrovascular disorders at the acute stage, which comprises administering the pyridinecarboxamide derivative represented by the formula (1) or a physiologically acceptable salt thereof to patients suffering from cerebrovascular disorders, especially cerebrovascular disorders at the acute stage.

Moreover, this invention relates to a method for the treatment of cerebral edema which comprises administering the pyridinecarboxamide derivative represented by the formula (1) or a physiologically acceptable salt thereof to patients suffering from cerebral edema.

The pyridinecarboxamide derivatives (1) of this invention have excellent inhibiting activity of cerebral edema, especially ischemic cerebral edema, and inhibiting activity of delayed neuronal death (inhibiting activity of Ca-influx in neuronal cells). Cerebral edema is the pathogenic condition accompanying cerebrovascular disorders, in particular, cerebrovascular disorders at the acute stage and then the pyridinecarboxamide derivatives (1) of this invention are useful as an inhibiting agent for cerebral edema or a therapeutic agent for cerebrovascular disorders. Moreover, the pyridinecarboxamide derivatives (1) of this invention have no hypotensive activity which has been considered as a side effect in the therapy of cerebrovascular disorders at the acute stage and hardly exert a behavior suppressing action and then they are excellent as a therapeutic agent for, in particular, cerebrovascular disorders at the acute stage. Moreover, the pyridinecarboxamide derivatives (1) of this invention have a cerebral protective action (an anti-anoxic action), an activity of increasing cerebral blood flow and an activity of inhibiting action on peroxidation of lipids and these actions may contribute to a far more increased utility of the pyridinecarboxamide derivatives (1) of this invention as a therapeutic agent for cerebrovascular disorders.

Almost all cerebrovascular disorders at the acute stage may accompany cerebral ischemia, which may accelerate microcirculation disorders around lesions to make cerebral disorders far worse.

Delayed neuronal death is meant to indicate the cell death wherein neuronal cells such as hippocampus CA fall off several days after a severe transient global cerebral ischemia due to temporal cardiac arrest and others. The mechanism of this action is believed to be an increase in glutamic acid and subsequent increase in intracellular calcium, and thus the pyridinecarboxamide derivatives of this invention, which can inhibit the delayed neuronal death, are useful as a therapeutic agent for cerebrovascular disorders.

Moreover, energy deficiency caused by ischemia or release of neurotransmitters such as glutamine and the like may cause influx of calcium ions into cells and generation of free radicals. Excessive production of free radicals may accelerate the formation of lipoperoxide and may cause irreversible disorders of cell membrane and rise in permeability of membrane, which leads to cerebral edema and neuronal death. Accordingly, the pyridinecarboxamide derivatives of the invention which inhibit the influx of calcium ions and the formation of lipoperoxide are useful as a therapeutic agent for cerebrovascular disorders at the acute stage.

The pathologic type of cerebrovascular disorders to which the therapeutic agent for cerebrovascular disorders of this invention may be applied includes cerebral hemorrhage, brain infarction (cerebral thrombosis, cerebral infarction), transient ischemic attack, subarachnoid hemorrhage and others. The cerebrovascular disorders at the acute stage as stated herein is meant to indicate the cerebrovascular disorders at the period of time of less than one month after the onset of cerebrovascular disorders.

The compounds (2) and compounds (3) of this invention are useful as intermediates for the synthesis of the pyridinecarboxamide derivatives (1).

In the pyridinecarboxamide derivatives represented by the formula (1), specific examples of the $C_1$–$C_4$ straight or branched alkyl group represented by R may be a methyl group, an ethyl group, a n-propyl group, a n-butyl group, an isopropyl group, an isobutyl group and a sec-butyl group, and specific examples of the group represented by the formula $(CH_2)_n$ may be a tetradecamethylene group, a pentadecamethylene group, a hexadecamethylene group, a heptadecamethylene group and an octadecamethylene group. In particular, a tetradecamethylene group, a hexadecamethylene group and an octadecamethylene group are preferable.

The pyridinecarboxamide derivatives represented by the formula (1) can be prepared by reacting the compounds of the formula (2) with a nitrating agent such as nitric acid, fuming nitric acid, tetrabutylammonium nitrate, strongly basic ion exchange resins (e.g., Amberlyst) of a nitrate form, silver nitrate or potassium nitrate in the presence or absence of a solvent at −40° C. to 120° C., preferably −40° C. to room temperature. As the solvent, there may be mentioned dichloromethane, chloroform, carbon tetrachloride, diethyl ether, tetrahydrofuran, toluene, acetonitrile, acetic anhydride, sulfuric acid and the like and a mixed solvent thereof. The pyridinecarboxamides represented by the formula (1) can be also prepared by reacting an alkali metal salt, halide or acid anhydride of the 6-piperazinyl-pyridine-3-carboxylic acid represented by the formula (3) with the ω-aminoalkyl nitrate represented by the formula (4).

The ω-aminoalkyl nitrates can be synthesized from an ω-aminoalkanol or a reactive derivative thereof, an ω-bromoalkylamine, an ω-iodoalkylamine, a methanesulfonic acid ω-aminoalkyl ester, a toluenesulfonic acid ω-aminoalkyl ester under the same condition as in the compounds of the formula (1).

The compounds (1) can be preferably produced by reacting a 6-(4-R-piperazinyl)pyridine-3-carboxylic acid sodium salt or a 6-(4-R-piperazinyl)-pyridine-3-carboxylic acid potassium salt with 0.5 to 4 equivalents of the compound of the ω-aminoalkyl nitrate (4) in a solvent in the presence of 0.5 to 4 equivalents of a condensing agent at −40° C. to 40° C., preferably −40° C. to room temperature. There may be incorporated in situ 0.5 to 4 equivalents of an additive and a base. As the solvent, there may be mentioned dichloromethane, chloroform, carbon tetrachloride, tetrahydrofuran, diethyl ether, dioxane, benzene, toluene, xylene, acetonitrile, dimethylformamide, dimethyl sulfoxide and the like and a mixed solvent thereof. As the condensing agent, there may be mentioned carbodiimides such as dicyclohexylcarbodiimide, 1-ethyl-3-(3-dimethylaminopropyl)carbodiimide hydrochloride and the like, azides such as diphenylphosphoryl azide and the like, carbonyldiimidazole, diethyl pyrocarbonate and the like. As the additive, there may be mentioned N-hydroxysuccinimide, 1-hydroxybenzotriazole and the like and, as the base, there may be mentioned organic bases such as triethylamine, diisopropylethylamine, pyridine and the like.

The compounds of the formula (2), wherein X is a bromine atom or an iodine atom may be synthesized by reacting the compounds wherein X is a hydroxyl group with hydrobromic acid or hydriodic acid.

The compounds of the formula (2) wherein X is a mesyloxy group or a tosyloxy group may be synthesized by reacting the compounds wherein X is a hydroxyl group with mesyl chloride or tosyl chloride in the presence of a base.

The compounds of the formula (2) can be synthesized by reacting a 6-piperazinylpyridine-3-carboxylic acid of the formula (3) or a reactive compound thereof such as an alkali metal salt thereof, for example, a sodium salt or potassium salt or halide thereof with a compound of the formula

$H_2N(CH_2)_nX$ (wherein n and X are as defined above) in a solvent in the presence of 0.5 to 4 equivalents of a condensing agent at a temperature from −40° C. to 40° C. There may be incorporated in situ 0.5 to 4 equivalents of an additive and a base. As the solvent, there may be mentioned dichloromethane, chloroform, carbon tetrachloride, tetrahydrofuran, diethyl ether, dioxane, benzene, toluene, xylene, acetonitrile, dimethylformamide, dimethyl sulfoxide and the like and a mixed solvent thereof. As the condensing agent, there may be mentioned carbodiimides such as dicyclohexylcarbodiimide, 1-ethyl-3-(3-dimethylaminopropyl)carbodiimide hydrochloride and the like, azides such as diphenylphosphoryl azide and the like, carbonyldiimidazole, diethyl pyrocarbonate and the like As the additive, there may be mentioned N-hydroxysuccinimide, 1-hydroxybenzotriazole and the like and, as the base, there may be mentioned organic bases such as triethylamine, diisopropylethylamine, pyridine and the like.

The compounds of the formula (2) wherein X is a hydroxyl group can be prepared by reacting a compound of the formula (5)

(5)

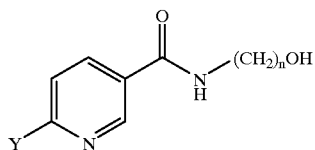

(wherein n is as defined above and Y is a halogen atom such as chlorine, bromine, iodine or the like) with 1 to 100 equivalents of a compound of the formula (6)

(6)

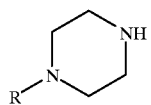

(wherein R is as defined above) in the presence or absence of a solvent at a temperature from room temperature to a reflux temperature or in a sealed tube. There may be also incorporated 0.05 to 10 equivalents of sodium iodide or potassium iodide in situ, or 0.5 to 10 equivalents of a base may be incorporated. As the solvent, there may be mentioned dichloromethane, chloroform, carbon tetrachloride, tetrahydrofuran, diethyl ether, dioxane, benzene, toluene, xylene, acetonitrile, dimethylformamide, dimethyl sulfoxide, methanol, ethanol and the like and a mixed solvent thereof. As the base, there may be mentioned inorganic bases such as sodium hydrogen carbonate, sodium carbonate, potassium carbonate, cesium carbonate and the like or organic bases such as triethylamine, diethylamine, diisopropylamine, diisopropylethylamine, pyridine and the like.

The compounds of the formula (2) can be also prepared by reacting the compound of the formula (5) with 1 to 100 equivalents of piperazine in the presence or absence of a solvent at a temperature from room temperature to a reflux temperature or in a sealed tube to form a compound of the formula (7)

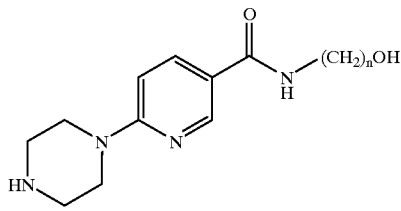
(7)

(wherein n is as defined above) and then reacting the compound of the formula (7) thus obtained with 1 to 10 equivalents of a compound of the formula RZ [wherein R is as defined above and Z represents a halogen atom such as chlorine, bromine, iodine and the like or a leaving group such as a sulfonate (e.g., a methanesulfonyloxy group, a toluenesulfonyloxy group)] in the presence or absence of a solvent at a temperature from room temperature to a reflux temperature or in a sealed tube. There may be also incorporated 0.05 to 4 equivalents of sodium iodide or potassium iodide in situ, or 0.5 to 10 equivalents of a base may be incorporated. As the solvent, there may be mentioned dichloromethane, chloroform, carbon tetrachloride, tetrahydrofuran, diethyl ether, dioxane, benzene, toluene, xylene, acetonitrile, dimethylformamide, dimethyl sulfoxide, methanol, ethanol and the like and a mixed solvent thereof. As the base, there may be mentioned inorganic bases such as sodium hydrogen carbonate, sodium carbonate, potassium carbonate, cesium carbonate and the like or organic bases such as triethylamine, diethylamine, diisopropylamine, diisopropylethylamine, pyridine and the like.

The compounds of the formula (5) can be prepared by reacting a compound of the formula (8)

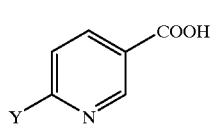
(8)

(wherein Y is as defined above) with 0.5 to 4 equivalents of a compound of the formula (9)

(wherein n is as defined above) in a solvent in the presence of 0.5 to 4 equivalents of a condensing agent at a temperature from −40° C. to 40° C. There may be incorporated in situ 0.5 to 4 equivalents of an additive and a base. As the solvent, there may be mentioned dichloromethane, chloroform, carbon tetrachloride, tetrahydrofuran, diethyl ether, dioxane, benzene, toluene, xylene, acetonitrile, dimethylformamide, dimethyl sulfoxide and the like and a mixed solvent thereof. As the condensing agent, there may be mentioned carbodiimides such as dicyclohexylcarbodiimide, 1-ethyl-3-(3-dimethylaminopropyl)carbodiimide hydrochloride and the like, azides such as diphenylphosphoryl azide and the like, carbonyldiimidazole, diethyl pyrocarbonate and the like. As the additive, there may be mentioned N-hydroxysucccinimide, 1-hydroxybenzotriazole and the like and, as the base, there may be mentioned organic bases such as triethylamine, diisopropylethylamine, pyridine and the like.

The compounds of the formula (5) can be also prepared by reacting a compound of the formula (10)

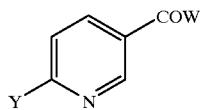
(10)

(wherein Y is as defined above and W represents a halogen atom such as chlorine, bromine, iodine and the like) with 0.5 to 4 equivalents of the compound of the formula (9) in a solvent at a temperature from −40° C. to 40° C. There may be incorporated in situ 0.5 to 4 equivalents of a base. As the solvent, there may be mentioned dichloromethane, chloroform, carbon tetrachloride, tetrahydrofuran, ether, dioxane, benzene, acetonitrile, dimethylformamide, dimethyl sulfoxide and the like and a mixed solvent thereof. As the base, there may be mentioned inorganic bases such as sodium hydrogen carbonate, sodium carbonate, potassium carbonate, cesium carbonate and the like or organic bases such as triethylamine, diethylamine, diisopropylamine, diisopropylethylamine, pyridine and the like.

The compound of the formula (12)

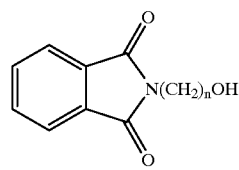
(12)

(wherein n is as defined above) is obtained by reacting a compound of the formula (11)

(wherein n is as defined above) with 0.2 to 2 equivalents of an azodicarboxylic acid ester, phosphine and phthalimide in a solvent at a temperature from −10° C. to 40° C. As the solvent, there may be mentioned dichloromethane, chloroform, carbon tetrachloride, tetrahydrofuran, ether, dioxane, benzene, acetonitrile, dimethylformamide, dimethyl sulfoxide and the like and a mixed solvent thereof. As the azodicarboxylic acid esters, there may be mentioned azodicarboxylic acid diethyl ester, azodicarboxylic acid diisopropyl ester and the like. As the phosphine, there may be mentioned triphenylphosphine, tributylphosphine and the like.

The compounds of the formula (12) can be also prepared by reacting the compound of the formula (11) with hydrobromic acid to form the monobrominated product (an ω-bromoalkanol) followed by reacting with potassium phthalimide.

The compounds of the formula (12) thus obtained may be allowed to react with an acid, a base or hydrazine in a solvent at a temperature of 0° C. to a reflux temperature to produce the compounds of the formula (9). As the solvent, there may be mentioned dichloromethane, chloroform, carbon tetrachloride, tetrahydrofuran, ether, dioxane, benzene, acetonitrile, dimethylformamide, dimethyl sulfoxide, methanol, ethanol, acetic acid, water and the like and a mixed solvent thereof. As the acid, there may be mentioned hydrochloric acid, sulfuric acid, acetic acid and the like and, as the base, sodium hydroxide, potassium hydroxide and the like.

The compounds of the formula (14)

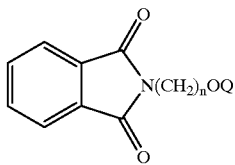
(14)

(wherein n and Q are as defined below) is obtained by reacting a compound of the formula (13)

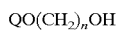

[wherein Q represents a protecting group such as a benzyl group, a substituted benzyl group (e.g., a p-methoxybenzyl group), an alkyl group (e.g., a methyl group or a tert-butyl group), a substituted methyl group (e.g., a methoxymethyl group), a substituted ethyl group (e.g., a 1-ethoxyethyl group), a silyl group (e.g., a triethylsilyl group or a tert-butyldimethylsilyl group) and an acyl group (e.g., an acetyl group or a benzoyl group), and n is as defined above for the general formula 7] with 0.2 to 2 equivalents of an azodicarboxylic acid ester, phosphine or phthalimide in a solvent at a temperature from −10° C. to 40° C. As the solvent, there may be mentioned dichloromethane, chloroform, carbon tetrachloride, tetrahydrofuran, ether, dioxane, benzene, acetonitrile, dimethylformamide, dimethyl sulfoxide and the like and a mixed solvent thereof. As the azodicarboxylic acid esters, there may be mentioned azodicarboxylic acid diethyl ester, azodicarboxylic acid diisopropyl ester and the like. As the phosphine, there may be mentioned triphenylphosphine, tributylphosphine and the like.

The compound of the formula (14) thus obtained may be converted to the formula (15)

(wherein n and Q are as defined above) by decomposing the N-phthalimide with an acid, base or hydrazine in a solvent at a temperature from 0° C. to a reflux temperature. As the solvent, there may be mentioned dichloromethane, chloroform, carbon tetrachloride, tetrahydrofuran, ether, dioxane, benzene, acetonitrile, dimethylformamide, dimethyl sulfoxide, methanol, ethanol, acetic acid, water and the like and a mixed solvent thereof. As the acid, there may be mentioned hydrochloric acid, sulfuric acid, acetic acid and the like and, as the base, sodium hydroxide, potassium hydroxide and the like.

By the deprotection of the protecting group in the compound of the formula (15) thus obtained, there can be prepared the compounds of the formula (9), but the deprotection may be carried out prior to the decomposition of the N-phthalimide. Deprotection reaction may be carried out under the conditions as conventionally applied in compliance with the type of the protecting group.

In the case where Q is a substituted benzyl group, the reaction may be carried out by the hydrogenation in the presence of a catalyst at a temperature from room temperature to a refluxing temperature. There may be incorporated in situ 1 to 10 equivalents of ammonium formate. As the solvent, there may be mentioned dichloromethane, chloroform, carbon tetrachloride, tetrahydrofuran, ether, dioxane, benzene, acetonitrile, dimethylformamide, dimethyl sulfoxide, methanol, ethanol, ethyl acetate, water and the like and a mixed solvent thereof, and, as the catalyst, palladium-carbon, platinum oxide, Raney nickel and the like.

In the case where Q is a substituted methyl group, the reaction may be carried out by reacting with an acid in the presence or absence of a solvent at a temperature from room temperature to a refluxing temperature. As the solvent, there may be mentioned dichloromethane, chloroform, carbon tetrachloride, tetrahydrofuran, ether, dioxane, benzene, acetonitrile, dimethylformamide, dimethyl sulfoxide, methanol, ethanol, ethyl acetate, water and the like and a mixed solvent thereof. As the acid, there may be mentioned hydrochloric acid, sulfuric acid, acetic acid, trifluoroacetic acid, p-toluenesulfonic acid and the like.

In the case where Q is a silyl group, the reaction may be carried out by reacting with an acid or a fluoride reagent at a temperature from 0° C. to 40° C. As the solvent, there may be mentioned dichloromethane, chloroform, carbon tetrachloride, tetrahydrofuran, ether, dioxane, benzene, acetonitrile, dimethylformamide, dimethyl sulfoxide, methanol, ethanol, ethyl acetate, water and the like and a mixed solvent thereof. As the acid, there may be mentioned hydrochloric acid, sulfuric acid, acetic acid, trifluoroacetic acid, p-toluenesulfonic acid and the like As the fluoride reagent, there may be mentioned hydrogen fluoride, potassium fluoride, tetrabutylammonium fluoride and the like.

In the case where Q is an acyl group, the reaction may be carried out by reacting with an acid or a base in a solvent at a temperature from 0° C. to a reflux temperature. As the solvent, there may be mentioned dichloromethane, chloroform, carbon tetrachloride, tetrahydrofuran, ether, dioxane, benzene, acetonitrile, dimethylformamide, dimethyl sulfoxide, methanol, ethanol, ethyl acetate, water and the like and a mixed solvent thereof. As the acid, there may be mentioned hydrochloric acid, sulfuric acid, acetic acid, trifluoroacetic acid, p-toluenesulfonic acid and the like As the base, there may be mentioned sodium hydroxide, potassium hydroxide, sodium hydrogen carbonate, sodium carbonate, potassium carbonate, cesium carbonate and the like.

The compound of the formula (17)

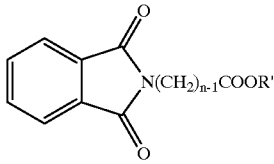
(17)

(wherein R' is a $C_1$–$C_6$ straight or branched alkyl group or a phenyl group and n is as defined above) is obtained by reacting a compound of the formula (16)

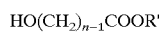

(wherein n and R' are as defined above) with 0.5 to 4 equivalents of an azodicarboxylic acid ester, phosphine and phthalimide in a solvent at a temperature from −10° C. to 40° C. As the solvent, there may be mentioned dichloromethane, chloroform, carbon tetrachloride, tetrahydrofuran, ether, dioxane, benzene, acetonitrile, dimethylformamide, dimethyl sulfoxide and the like and a mixed solvent thereof. As the azodicarboxylic acid esters, there may be mentioned azocarboxylic acid diethyl ester, azocarboxylic acid diisopropyl ester and the like. As the phosphine, there may be mentioned triphenylphosphine, tributylphosphine and the like.

The compound of the formula (17) is converted to the formula (18)

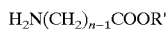

$$H_2N(CH_2)_{n-1}COOR'$$

(wherein n and R' are as defined above) by decomposing the N-phthalimide in a solvent with an acid, a base or a hydrazine at a temperature of 0° C. to a reflux temperature. As the solvent, there may be mentioned dichloromethane, chloroform, carbon tetrachloride, tetrahydrofuran, ether, dioxane, benzene, acetonitrile, dimethylformamide, dimethyl sulfoxide, methanol, ethanol, acetic acid, water and the like and a mixed solvent thereof. As the acid, there may be mentioned hydrochloric acid, sulfuric acid, acetic acid and the like As the base, there may be mentioned sodium hydroxide, potassium hydroxide and the like.

The compound (9) can be prepared by treating the compound (18) in a solvent in the presence of a reducing agent at a temperature from −78° C. to a reflux temperature. This step may be carried out prior to the decomposition of the N-phthalimide. As the solvent, there may be mentioned dichloromethane, chloroform, carbon tetrachloride, tetrahydrofuran, ether, dioxane, benzene, toluene, xylene and the like and a mixed solvent thereof. As the reducing agent, there may be mentioned aluminum reagents such as lithium aluminum hydride, diisobutylaluminum and the like or diborane and the like.

The compound (13) can be prepared by reacting the compound (11) with 0.2 to 2 equivalents of QX' (wherein X' is halogen such as chlorine, bromine, iodine and the like or a leaving group such as sulfonate and the like and Q is as defined above) in a solvent in the presence of 0.2 to 2 equivalents of a base at a temperature from 0° C. to a reflux temperature. As the solvent, there may be mentioned dichloromethane, chloroform, carbon tetrachloride, tetrahydrofuran, diethyl ether, dioxane, benzene, toluene, xylene, acetonitrile, dimethylformamide, dimethyl sulfoxide and the like and a mixed solvent thereof. As the base, there may be mentioned inorganic bases such as sodium hydrogen carbonate, sodium carbonate, potassium carbonate, cesium carbonate and the like or organic bases such as triethylamine, diethylamine, diisopropylamine, diisopropylethylamine, pyridine, imidazole and the like.

The compound of the formula (19)

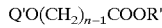

$$Q'O(CH_2)_{n-1}COOR'$$

[wherein n and R' are as defined above and Q' represents a benzyl group, a substituted benzyl group (e.g., a p-methoxybenzyl group), an alkyl group (e.g., a methyl group or a tert-butyl group), a substituted methyl group (e.g., a methoxymethyl group), a substituted ethyl group (e.g., a 1-ethoxyethyl group) and a silyl group (e.g., a triethylsilyl group or a tert-butyldimethylsilyl group)] is obtained by reacting the compound (16) with 0.2 to 2 equivalents of Q'X' [wherein X' is halogen such as chlorine, bromine, iodine and the like or a leaving group such as sulfonate and the like and Q is as defined above and Q' represents a benzyl group, a substituted benzyl group (e.g., a p-methoxybenzyl group), an alkyl group (e.g., a methyl group or a tert-butyl group), a substituted methyl group (e.g., a methoxymethyl group), a substituted ethyl group (e.g., a 1-ethoxyethyl group) and a silyl group (e.g., a triethylsilyl group or a tert-butyldimethylsilyl group)] in a solvent in the presence of 0.2 to 2 equivalents of a base at a temperature from 0° C. to a reflux temperature. As the solvent, there may be mentioned dichloromethane, chloroform, carbon tetrachloride, tetrahydrofuran, diethyl ether, dioxane, benzene, toluene, xylene, acetonitrile, dimethylformamide, dimethyl sulfoxide and the like and a mixed solvent thereof. As the base, there may be mentioned inorganic bases such as sodium hydrogen carbonate, sodium carbonate, potassium carbonate, cesium carbonate and the like or organic bases such as triethylamine, diethylamine, diisopropylamine, diisopropylethylamine, pyridine, imidazole and the like.

The compound (13) can be prepared by treating the compound (19) in a solvent in the presence of a reducing agent at a temperature from −78° C. to a reflux temperature. As the solvent, there may be mentioned dichloromethane, chloroform, carbon tetrachloride, tetrahydrofuran, ether, dioxane, benzene, toluene, xylene and the like and a mixed solvent thereof. As the reducing agent, there may be mentioned aluminum reagents such as lithium aluminum hydride, diisobutylaluminum and the like or diborane and the like.

Specific examples of the compounds of the formula (1) are given below:

N-(14-nitroxytetradecyl)-6-(1-piperazinyl)pyridine-3-carboxamide,

N-(14-nitroxytetradecyl)-6-(4-methyl-1-piperazinyl)pyridine-3-carboxamide,

N-(14-nitroxytetradecyl)-6-(4-ethyl-1-piperazinyl)pyridine-3-carboxamide,

N-(14-nitroxytetradecyl)-6-(4-propyl-1-piperazinyl)pyridine-3-carboxamide,

N-(14-nitroxytetradecyl)-6-(4-isopropyl-1-piperazinyl)pyridine-3-carboxamide,

N-(14-nitroxytetradecyl)-6-(4-butyl-1-piperazinyl)pyridine-3-carboxamide,

N-(14-nitroxytetradecyl)-6-(4-isobutyl-1-piperazinyl)pyridine-3-carboxamide,

N-(14-nitroxytetradecyl)-6-(4-sec-butyl-1-piperazinyl)pyridine-3-carboxamide,

N-(15-nitroxypentadecyl)-6-(1-piperazinyl)pyridine-3-carboxamide,

N-(15-nitroxypentadecyl)-6-(4-methyl-1-piperazinyl)pyridine-3-carboxamide,

N-(15-nitroxypentadecyl)-6-(4-ethyl-1-piperazinyl)pyridine-3-carboxamide,

N-(15-nitroxypentadecyl)-6-(4-propyl-1-piperazinyl)pyridine-3-carboxamide,

N-(15-nitroxypentadecyl)-6-(4-isopropyl-1-piperazinyl)pyridine-3-carboxamide,

N-(15-nitroxypentadecyl)-6-(4-butyl-1-piperazinyl)pyridine-3-carboxamide,

N-(15-nitroxypentadecyl)-6-(4-isobutyl-1-piperazinyl)pyridine-3-carboxamide,

N-(15-nitroxypentadecyl)-6-(4-sec-butyl-1-piperazinyl)pyridine-3-carboxamide,

N-(16-nitroxyhexadecyl)-6-(1-piperazinyl)pyridine-3-carboxamide,

N-(16-nitroxyhexadecyl)-6-(4-methyl-1-piperazinyl)pyridine-3-carboxamide,
N-(16-nitroxyhexadecyl)-6-(4-ethyl-1-piperazinyl)pyridine-3-carboxamide,
N-(16-nitroxyhexadecyl)-6-(4-propyl-1-piperazinyl)pyridine-3-carboxamide,
N-(16-nitroxyhexadecyl)-6-(4-isopropyl-1-piperazinyl)pyridine-3-carboxamide,
N-(16-nitroxyhexadecyl)-6-(4-butyl-1-piperazinyl)pyridine-3-carboxamide,
N-(16-nitroxyhexadecyl)-6-(4-isobutyl-1-piperazinyl)pyridine-3-carboxamide,
N-(16-nitroxyhexadecyl)-6-(4-sec-butyl-1-piperazinyl)pyridine-3-carboxamide,
N-(17-nitroxyheptadecyl)-6-(1-piperazinyl)pyridine-3-carboxamide,
N-(17-nitroxyheptadecyl)-6-(4-methyl-1-piperazinyl)pyridine-3-carboxamide,
N-(17-nitroxyheptadecyl)-6-(4-ethyl-1-piperazinyl)pyridine-3-carboxamide,
N-(17-nitroxyheptadecyl)-6-(4-propyl-1-piperazinyl)pyridine-3-carboxamide,
N-(17-nitroxyheptadecyl)-6-(4-isopropyl-1-piperazinyl)pyridine-3-carboxamide,
N-(17-nitroxyheptadecyl)-6-(4-butyl-1-piperazinyl)pyridine-3-carboxamide,
N-(17-nitroxyheptadecyl)-6-(4-isobutyl-1-piperazinyl)pyridine-3-carboxamide,
N-(17-nitroxyheptadecyl)-6-(4-sec-butyl-1-piperazinyl)pyridine-3-carboxamide,
N-(18-nitroxyoctadecyl)-6-(1-piperazinyl)pyridine-3-carboxamide,
N-(18-nitroxyoctadecyl)-6-(4-methyl-1-piperazinyl)pyridine-3-carboxamide,
N-(18-nitroxyoctadecyl)-6-(4-ethyl-1-piperazinyl)pyridine-3-carboxamide,
N-(18-nitroxyoctadecyl)-6-(4-propyl-1-piperazinyl)pyridine-3-carboxamide,
N-(18-nitroxyoctadecyl)-6-(4-isopropyl-1-piperazinyl)pyridine-3-carboxamide,
N-(18-nitroxyoctadecyl)-6-(4-butyl-1-piperazinyl)pyridine-3-carboxamide,
N-(18-nitroxyoctadecyl)-6-(4-isobutyl-1-piperazinyl)pyridine-3-carboxamide,
N-(18-nitroxyoctadecyl)-6-(4-sec-butyl-1-piperazinyl)pyridine-3-carboxamide.

Specific examples of the compounds of the formula (2) are given below:
N-(14-hydroxytetradecyl)-6-(1-piperazinyl)pyridine-3-carboxamide,
N-(14-hydroxytetradecyl)-6-(4-methyl-1-piperazinyl)pyridine-3-carboxamide,
N-(14-hydroxytetradecyl)-6-(4-ethyl-1-piperazinyl)pyridine-3-carboxamide,
N-(14-hydroxytetradecyl)-6-(4-propyl-1-piperazinyl)pyridine-3-carboxamide,
N-(14-hydroxytetradecyl)-6-(4-isopropyl-1-piperazinyl)pyridine-3-carboxamide,
N-(14-hydroxytetradecyl)-6-(4-butyl-1-piperazinyl)pyridine-3-carboxamide,
N-(14-hydroxytetradecyl)-6-(4-isobutyl-1-piperazinyl)pyridine-3-carboxamide,
N-(14-hydroxytetradecyl)-6-(4-sec-butyl-1-piperazinyl)pyridine-3-carboxamide,
N-(15-hydroxypentadecyl)-6-(1-piperazinyl)pyridine-3-carboxamide,
N-(15-hydroxypentadecyl)-6-(4-methyl-1-piperazinyl)pyridine-3-carboxamide,
N-(15-hydroxypentadecyl)-6-(4-ethyl-1-piperazinyl)pyridine-3-carboxamide,
N-(15-hydroxypentadecyl)-6-(4-propyl-1-piperazinyl)pyridine-3-carboxamide,
N-(15-hydroxypentadecyl)-6-(4-isopropyl-1-piperazinyl)pyridine-3-carboxamide,
N-(15-hydroxypentadecyl)-6-(4-butyl-1-piperazinyl)pyridine-3-carboxamide,
N-(15-hydroxypentadecyl)-6-(4-isobutyl-1-piperazinyl)pyridine-3-carboxamide,
N-(15-hydroxypentadecyl)-6-(4-sec-butyl-1-piperazinyl)pyridine-3-carboxamide,
N-(16-hydroxyhexadecyl)-6-(1-piperazinyl)pyridine-3-carboxamide,
N-(16-hydroxyhexadecyl)-6-(4-methyl-1-piperazinyl)pyridine-3-carboxamide,
N-(16-hydroxyhexadecyl)-6-(4-ethyl-1-piperazinyl)pyridine-3-carboxamide,
N-(16-hydroxyhexadecyl)-6-(4-propyl-1-piperazinyl)pyridine-3-carboxamide,
N-(16-hydroxyhexadecyl)-6-(4-isopropyl-1-piperazinyl)pyridine-3-carboxamide,
N-(16-hydroxyhexadecyl)-6-(4-butyl-1-piperazinyl)pyridine-3-carboxamide,
N-(16-hydroxyhexadecyl)-6-(4-isobutyl-1-piperazinyl)pyridine-3-carboxamide,
N-(16-hydroxyhexadecyl)-6-(4-sec-butyl-1-piperazinyl)pyridine-3-carboxamide,
N-(17-hydroxyheptadecyl)-6-(1-piperazinyl)pyridine-3-carboxamide,
N-(17-hydroxyheptadecyl)-6-(4-methyl-1-piperazinyl)pyridine-3-carboxamide,
N-(17-hydroxyheptadecyl)-6-(4-ethyl-1-piperazinyl)pyridine-3-carboxamide,
N-(17-hydroxyheptadecyl)-6-(4-propyl-1-piperazinyl)pyridine-3-carboxamide,
N-(17-hydroxyheptadecyl)-6-(4-isopropyl-1-piperazinyl)pyridine-3-carboxamide,
N-(17-hydroxyheptadecyl)-6-(4-butyl-1-piperazinyl)pyridine-3-carboxamide,
N-(17-hydroxyheptadecyl)-6-(4-isobutyl-1-piperazinyl)pyridine-3-carboxamide,
N-(17-hydroxyheptadecyl)-6-(4-sec-butyl-1-piperazinyl)pyridine-3-carboxamide,
N-(18-hydroxyoctadecyl)-6-(1-piperazinyl)pyridine-3-carboxamide,
N-(18-hydroxyoctadecyl)-6-(4-methyl-1-piperazinyl)pyridine-3-carboxamide,
N-(18-hydroxyoctadecyl)-6-(4-ethyl-1-piperazinyl)pyridine-3-carboxamide,
N-(18-hydroxyoctadecyl)-6-(4-propyl-1-piperazinyl)pyridine-3-carboxamide,
N-(18-hydroxyoctadecyl)-6-(4-isopropyl-1-piperazinyl)pyridine-3-carboxamide,
N-(18-hydroxyoctadecyl)-6-(4-butyl-1-piperazinyl)pyridine-3-carboxamide, N-(18-hydroxyoctadecyl)-6-(4-isobutyl-1-piperazinyl)pyridine-3-carboxamide,
N-(18-hydroxyoctadecyl)-6-(4-sec-butyl-1-piperazinyl)pyridine-3-carboxamide,
N-(14-iodotetradecyl)-6-(1-piperazinyl)pyridine-3-carboxamide,
N-(14-iodotetradecyl)-6-(4-methyl-1-piperazinyl)pyridine-3-carboxamide,
N-(14-iodotetradecyl)-6-(4-ethyl-1-piperazinyl)pyridine-3-carboxamide,
N-(14-iodotetradecyl)-6-(4-propyl-1-piperazinyl)pyridine-3-carboxamide,
N-(14-iodotetradecyl)-6-(4-isopropyl-1-piperazinyl)pyridine-3-carboxamide,
N-(14-iodotetradecyl)-6-(4-butyl-1-piperazinyl)pyridine-3-carboxamide,
N-(14-iodotetradecyl)-6-(4-isobutyl-1-piperazinyl)pyridine-3-carboxamide,
N-(14-iodotetradecyl)-6-(4-sec-butyl-1-piperazinyl)pyridine-3-carboxamide,
N-(15-iodopentadecyl)-6-(1-piperazinyl)pyridine-3-carboxamide,
N-(15-iodopentadecyl)-6-(4-methyl-1-piperazinyl)pyridine-3-carboxamide,
N-(15-iodopentadecyl)-6-(4-ethyl-1-piperazinyl)pyridine-3-carboxamide,
N-(15-iodopentadecyl)-6-(4-propyl-1-piperazinyl)pyridine-3-carboxamide,
N-(15-iodopentadecyl)-6-(4-isopropyl-1-piperazinyl)pyridine-3-carboxamide,
N-(15-iodopentadecyl)-6-(4-butyl-1-piperazinyl)pyridine-3-carboxamide,
N-(15-iodopentadecyl)-6-(4-isobutyl-1-piperazinyl)pyridine-3-carboxamide,
N-(15-iodopentadecyl)-6-(4-sec-butyl-1-piperazinyl)pyridine-3-carboxamide,
N-(16-iodohexadecyl)-6-(1-piperazinyl)pyridine-3-carboxamide,
N-(16-iodohexadecyl)-6-(4-methyl-1-piperazinyl)pyridine-3-carboxamide,
N-(16-iodohexadecyl)-6-(4-ethyl-1-piperazinyl)pyridine-3-carboxamide,
N-(16-iodohexadecyl)-6-(4-propyl-1-piperazinyl)pyridine-3-carboxamide,
N-(16-iodohexadecyl)-6-(4-isopropyl-1-piperazinyl)pyridine-3-carboxamide,
N-(16-iodohexadecyl)-6-(4-butyl-1-piperazinyl)pyridine-3-carboxamide,
N-(16-iodohexadecyl)-6-(4-isobutyl-1-piperazinyl)pyridine-3-carboxamide,
N-(16-iodohexadecyl)-6-(4-sec-butyl-1-piperazinyl)pyridine-3-carboxamide,
N-(17-iodoheptadecyl)-6-(1-piperazinyl)pyridine-3-carboxamide,
N-(17-iodoheptadecyl)-6-(4-methyl-1-piperazinyl)pyridine-3-carboxamide,
N-(17-iodoheptadecyl)-6-(4-ethyl-1-piperazinyl)pyridine-3-carboxamide,
N-(17-iodoheptadecyl)-6-(4-propyl-1-piperazinyl)pyridine-3-carboxamide,
N-(17-iodoheptadecyl)-6-(4-isopropyl-1-piperazinyl)pyridine-3-carboxamide,
N-(17-iodoheptadecyl)-6-(4-butyl-1-piperazinyl)pyridine-3-carboxamide,
N-(17-iodoheptadecyl)-6-(4-isobutyl-1-piperazinyl)pyridine-3-carboxamide,
N-(17-iodoheptadecyl)-6-(4-sec-butyl-1-piperazinyl)pyridine-3-carboxamide,
N-(18-iodooctadecyl)-6-(1-piperazinyl)pyridine-3-carboxamide,
N-(18-iodooctadecyl)-6-(4-methyl-1-piperazinyl)pyridine-3-carboxamide,
N-(18-iodooctadecyl)-6-(4-ethyl-1-piperazinyl)pyridine-3-carboxamide,
N-(18-iodooctadecyl)-6-(4-propyl-1-piperazinyl)pyridine-3-carboxamide,
N-(18-iodooctadecyl)-6-(4-isopropyl-1-piperazinyl)pyridine-3-carboxamide,
N-(18-iodooctadecyl)-6-(4-butyl-1-piperazinyl)pyridine-3-carboxamide,
N-(18-iodooctadecyl)-6-(4-isobutyl-1-piperazinyl)pyridine-3-carboxamide,
N-(18-iodooctadecyl)-6-(4-sec-butyl-1-piperazinyl)pyridine-3-carboxamide,
N-(14-bromotetradecyl)-6-(1-piperazinyl)pyridine-3-carboxamide,
N-(14-bromotetradecyl)-6-(4-methyl-1-piperazinyl)pyridine-3-carboxamide,
N-(14-bromotetradecyl)-6-(4-ethyl-1-piperazinyl)pyridine-3-carboxamide,
N-(14-bromotetradecyl)-6-(4-propyl-1-piperazinyl)pyridine-3-carboxamide,
N-(14-bromotetradecyl)-6-(4-isopropyl-1-piperazinyl)pyridine-3-carboxamide,
N-(14-bromotetradecyl)-6-(4-butyl-1-piperazinyl)pyridine-3-carboxamide,
N-(14-bromotetradecyl)-6-(4-isobutyl-1-piperazinyl)pyridine-3-carboxamide,
N-(14-bromotetradecyl)-6-(4-sec-butyl-1-piperazinyl)pyridine-3-carboxamide,
N-(15-bromopentadecyl)-6-(1-piperazinyl)pyridine-3-carboxamide,
N-(15-bromopentadecyl)-6-(4-methyl-1-piperazinyl)pyridine-3-carboxamide,
N-(15-bromopentadecyl)-6-(4-ethyl-1-piperazinyl)pyridine-3-carboxamide,
N-(15-bromopentadecyl)-6-(4-propyl-1-piperazinyl)pyridine-3-carboxamide,
N-(15-bromopentadecyl)-6-(4-isopropyl-1-piperazinyl)pyridine-3-carboxamide,
N-(15-bromopentadecyl)-6-(4-butyl-1-piperazinyl)pyridine-3-carboxamide,
N-(15-bromopentadecyl)-6-(4-isobutyl-1-piperazinyl)pyridine-3-carboxamide,
N-(15-bromopentadecyl)-6-(4-sec-butyl-1-piperazinyl)pyridine-3-carboxamide,
N-(16-bromohexadecyl)-6-(1-piperazinyl)pyridine-3-carboxamide,
N-(16-bromohexadecyl)-6-(4-methyl-1-piperazinyl)pyridine-3-carboxamide,
N-(16-bromohexadecyl)-6-(4-ethyl-1-piperazinyl)pyridine-3-carboxamide,
N-(16-bromohexadecyl)-6-(4-propyl-1-piperazinyl)pyridine-3-carboxamide, N-(16-bromohexadecyl)-6-(4-isopropyl-1-piperazinyl)pyridine-3-carboxamide,
N-(16-bromohexadecyl)-6-(4-butyl-1-piperazinyl)pyridine-3-carboxamide,
N-(16-bromohexadecyl)-6-(4-isobutyl-1-piperazinyl)pyridine-3-carboxamide,
N-(16-bromohexadecyl)-6-(4-sec-butyl-1-piperazinyl)pyridine-3-carboxamide,
N-(17-bromoheptadecyl)-6-(1-piperazinyl)pyridine-3-carboxamide,
N-(17-bromoheptadecyl)-6-(4-methyl-1-piperazinyl)pyridine-3-carboxamide,
N-(17-bromoheptadecyl)-6-(4-ethyl-1-piperazinyl)pyridine-3-carboxamide,
N-(17-bromoheptadecyl)-6-(4-propyl-1-piperazinyl)pyridine-3-carboxamide,
N-(17-bromoheptadecyl)-6-(4-isopropyl-1-piperazinyl)pyridine-3-carboxamide,
N-(17-bromoheptadecyl)-6-(4-butyl-1-piperazinyl)pyridine-3-carboxamide,
N-(17-bromoheptadecyl)-6-(4-isobutyl-1-piperazinyl)pyridine-3-carboxamide,
N-(17-bromoheptadecyl)-6-(4-sec-butyl-1-piperazinyl)pyridine-3-carboxamide,
N-(18-bromooctadecyl)-6-(1-piperazinyl)pyridine-3-carboxamide,
N-(18-bromooctadecyl)-6-(4-methyl-1-piperazinyl)pyridine-3-carboxamide,
N-(18-bromooctadecyl)-6-(4-ethyl-1-piperazinyl)pyridine-3-carboxamide,
N-(18-bromooctadecyl)-6-(4-propyl-1-piperazinyl)pyridine-3-carboxamide,
N-(18-bromooctadecyl)-6-(4-isopropyl-1-piperazinyl)pyridine-3-carboxamide,
N-(18-bromooctadecyl)-6-(4-butyl-1-piperazinyl)pyridine-3-carboxamide,
N-(18-bromooctadecyl)-6-(4-isobutyl-1-piperazinyl)pyridine-3-carboxamide,
N-(18-bromooctadecyl)-6-(4-sec-butyl-1-piperazinyl)pyridine-3-carboxamide,
N-(14-mesyloxytetradecyl)-6-(1-piperazinyl)pyridine-3-carboxamide,
N-(14-mesyloxytetradecyl)-6-(4-methyl-1-piperazinyl)pyridine-3-carboxamide,
N-(14-mesyloxytetradecyl)-6-(4-ethyl-1-piperazinyl)pyridine-3-carboxamide,
N-(14-mesyloxytetradecyl)-6-(4-propyl-1-piperazinyl)pyridine-3-carboxamide,
N-(14-mesyoxytetradecyl)-6-(4-isopropyl-1-piperazinyl)pyridine-3-carboxamide,
N-(14-mesyloxytetradecyl)-6-(4-butyl-1-piperazinyl)pyridine-3-carboxamide,
N-(14-mesyloxytetradecyl)-6-(4-isobutyl-1-piperazinyl)pyridine-3-carboxamide,
N-(14-mesyloxytetradecyl)-6-(4-sec-butyl-1-piperazinyl)pyridine-3-carboxamide,
N-(15-mesyloxypentadecyl)-6-(1-piperazinyl)pyridine-3-carboxamide,
N-(15-mesyloxypentadecyl)-6-(4-methyl-1-piperazinyl)pyridine-3-carboxamide,
N-(15-mesyloxypentadecyl)-6-(4-ethyl-1-piperazinyl)pyridine-3-carboxamide,
N-(15-mesylpentadecyl)-6-(4-propyl-1-piperazinyl)pyridine-3-carboxamide,
N-(15-mesyloxypentadecyl)-6-(4-isopropyl-1-piperazinyl)pyridine-3-carboxamide,
N-(15-mesyloxypentadecyl)-6-(4-butyl-1-piperazinyl)pyridine-3-carboxamide,
N-(15-mesyloxypentadecyl)-6-(4-isobutyl-1-piperazinyl)pyridine-3-carboxamide,
N-(15-mesyloxypentadecyl)-6-(4-sec-butyl-1-piperazinyl)pyridine-3-carboxamide,
N-(16-mesyloxyhexadecyl)-6-(1-piperazinyl)pyridine-3-carboxamide,
N-(16-mesyloxyhexadecyl)-6-(4-methyl-1-piperazinyl)pyridine-3-carboxamide,
N-(16-mesyloxyhexadecyl)-6-(4-ethyl-1-piperazinyl)pyridine-3-carboxamide,
N-(16-mesyloxyhexadecyl)-6-(4-propyl-1-piperazinyl)pyridine-3-carboxamide,
N-(16-mesyloxyhexadecyl)-6-(4-isopropyl-1-piperazinyl)pyridine-3-carboxamide,
N-(16-mesyloxyhexadecyl)-6-(4-butyl-1-piperazinyl)pyridine-3-carboxamide,
N-(16-mesyloxyhexadecyl)-6-(4-isobutyl-1-piperazinyl)pyridine-3-carboxamide,
N-(16-mesyloxyhexadecyl)-6-(4-sec-butyl-1-piperazinyl)pyridine-3-carboxamide,
N-(17-mesyloxyheptadecyl)-6-(1-piperazinyl)pyridine-3-carboxamide,
N-(17-mesyloxyheptadecyl)-6-(4-methyl-1-piperazinyl)pyridine-3-carboxamide,
N-(17-mesyloxyheptadecyl)-6-(4-ethyl-1-piperazinyl)pyridine-3-carboxamide,
N-(17-mesyloxyheptadecyl)-6-(4-propyl-1-piperazinyl)pyridine-3-carboxamide,
N-(17-mesyloxyheptadecyl)-6-(4-isopropyl-1-piperazinyl)pyridine-3-carboxamide,
N-(17-mesyloxyheptadecyl)-6-(4-butyl-1-piperazinyl)pyridine-3-carboxamide,
N-(17-mesyloxyheptadecyl)-6-(4-isobutyl-1-piperazinyl)pyridine-3-carboxamide,
N-(17-mesyloxyheptadecyl)-6-(4-sec-butyl-1-piperazinyl)pyridine-3-carboxamide,
N-(18-mesyloxyoctadecyl)-6-(1-piperazinyl)pyridine-3-carboxamide,
N-(18-mesyloxyoctadecyl)-6-(4-methyl-1-piperazinyl)pyridine-3-carboxamide,
N-(18-mesyloxyoctadecyl)-6-(4-ethyl-1-piperazinyl)pyridine-3-carboxamide,
N-(18-mesyloxyoctadecyl)-6-(4-propyl-1-piperazinyl)pyridine-3-carboxamide,
N-(18-mesyloxyoctadecyl)-6-(4-isopropyl-1-piperazinyl)pyridine-3-carboxamide,
N-(18-mesyloxyoctadecyl)-6-(4-butyl-1-piperazinyl)pyridine-3-carboxamide,
N-(18-mesyloxyoctadecyl)-6-(4-isobutyl-1-piperazinyl)pyridine-3-carboxamide,
N-(18-mesyloxyoctadecyl)-6-(4-sec-butyl-1-piperazinyl)pyridine-3-carboxamide,
N-(14-tosyloxytetradecyl)-6-(1-piperazinyl)pyridine-3-carboxamide,
N-(14-tosyloxytetradecyl)-6-(4-methyl-1-piperazinyl)pyridine-3-carboxamide, N-(14-tosyloxytetradecyl)-6-(4-ethyl-1-piperazinyl)pyridine-3-carboxamide,
N-(14-tosyloxytetradecyl)-6-(4-propyl-1-piperazinyl)pyridine-3-carboxamide,
N-(14-tosyltetradecyl)-6-(4-isopropyl-1-piperazinyl)pyridine-3-carboxamide,
N-(14-tosyloxytetradecyl)-6-(4-butyl-1-piperazinyl)pyridine-3-carboxamide,
N-(14-tosyloxytetradecyl)-6-(4-isobutyl-1-piperazinyl)pyridine-3-carboxamide,
N-(14-tosyloxytetradecyl)-6-(4-sec-butyl-1-piperazinyl)pyridine-3-carboxamide,
N-(15-tosyloxypentadecyl)-6-(1-piperazinyl)pyridine-3-carboxamide,
N-(15-tosyloxypentadecyl)-6-(4-methyl-1-piperazinyl)pyridine-3-carboxamide,
N-(15-tosyloxypentadecyl)-6-(4-ethyl-1-piperazinyl)pyridine-3-carboxamide,
N-(15-tosylpentadecyl)-6-(4-propyl-1-piperazinyl)pyridine-3-carboxamide,
N-(15-tosyloxypentadecyl)-6-(4-isopropyl-1-piperazinyl)pyridine-3-carboxamide,
N-(15-tosyloxypentadecyl)-6-(4-butyl-1-piperazinyl)pyridine-3-carboxamide,
N-(15-tosyloxypentadecyl)-6-(4-isobutyl-1-piperazinyl)pyridine-3-carboxamide,
N-(15-tosyloxypentadecyl)-6-(4-sec-butyl-1-piperazinyl)pyridine-3-carboxamide,
N-(16-tosyloxyhexadecyl)-6-(1-piperazinyl)pyridine-3-carboxamide,
N-(16-tosyloxyhexadecyl)-6-(4-methyl-1-piperazinyl)pyridine-3-carboxamide,
N-(16-tosyloxyhexadecyl)-6-(4-ethyl-1-piperazinyl)pyridine-3-carboxamide,
N-(16-tosyloxyhexadecyl)-6-(4-propyl-1-piperazinyl)pyridine-3-carboxamide,
N-(16-tosyloxyhexadecyl)-6-(4-isopropyl-1-piperazinyl)pyridine-3-carboxamide,
N-(16-tosyloxyhexadecyl)-6-(4-butyl-1-piperazinyl)pyridine-3- carboxamide,
N-(16-tosyloxyhexadecyl)-6-(4-isobutyl-1-piperazinyl)pyridine-3-carboxamide,
N-(16-tosyloxyhexadecyl)-6-(4-sec-butyl-1-piperazinyl)pyridine-3-carboxamide,
N-(17-tosyloxyheptadecyl)-6-(1-piperazinyl)pyridine-3-carboxamide,
N-(17-tosyloxyheptadecyl)-6-(4-methyl-1-piperazinyl)pyridine-3-carboxamide,
N-(17-tosyloxyheptadecyl)-6-(4-ethyl-1-piperazinyl)pyridine-3-carboxamide,
N-(17-tosyloxyheptadecyl)-6-(4-propyl-1-piperazinyl)pyridine-3-carboxamide,
N-(17-tosyloxyheptadecyl)-6-(4-isopropyl-1-piperazinyl)pyridine-3-carboxamide,
N-(17-tosyloxyheptadecyl)-6-(4-butyl-1-piperazinyl)pyridine-3-carboxamide,
N-(17-tosyloxyheptadecyl)-6-(4-isobutyl-1-piperazinyl)pyridine-3-carboxamide,
N-(17-tosyloxyheptadecyl)-6-(4-sec-butyl-1-piperazinyl)pyridine-3-carboxamide,
N-(18-tosyloxyoctadecyl)-6-(1-piperazinyl)pyridine-3-carboxamide,
N-(18-tosyloxyoctadecyl)-6-(4-methyl-1-piperazinyl)pyridine-3-carboxamide,
N-(18-tosyloxyoctadecyl)-6-(4-ethyl-1-piperazinyl)pyridine-3-carboxamide,
N-(18-tosyloxyoctadecyl)-6-(4-propyl-1-piperazinyl)pyridine-3-carboxamide,
N-(18-tosyloxyoctadecyl)-6-(4-isopropyl-1-piperazinyl)pyridine-3-carboxamide,
N-(18-tosyloxyoctadecyl)-6-(4-butyl-1-piperazinyl)pyridine-3-carboxamide,
N-(18-tosyloxyoctadecyl)-6-(4-isobutyl-1-piperazinyl)pyridine-3-carboxamide,
N-(18-tosyloxyoctadecyl)-6-(4-sec-butyl-1-piperazinyl)pyridine-3-carboxamide.

Specific examples of the ω-aminoalkyl nitrate of the formula (4) are given below.

14-Aminotetradecyl nitrate,
15-aminopentadecyl nitrate,
16-aminohexadecyl nitrate,
18-aminooctadecyl nitrate.

Specific examples of the compounds of the formula (5) are given below.

N-(14-hydroxytetradecyl)-6-chloropyridine-3-carboxamide,
N-(15-hydroxypentadecyl)-6-chloropyridine-3-carboxamide,
N-(16-hydroxyhexadecyl)-6-chloropyridine-3-carboxamide,
N-(17-hydroxyheptadecyl)-6-chloropyridine-3-carboxamide,
N-(18-hydroxyoctadecyl)-6-chloropyridine-3-carboxamide,
N-(13-hydroxytridecyl)-6-bromopyridine-3-carboxamide,
N-(14-hydroxytetradecyl)-6-bromopyridine-3-carboxamide,
N-(15-hydroxypentadecyl)-6-bromopyridine-3-carboxamide,
N-(16-hydroxyhexadecyl)-6-bromopyridine-3-carboxamide,
N-(17-hydroxyheptadecyl)-6-bromopyridine-3-carboxamide,
N-(18-hydroxyoctadecyl)-6-bromopyridine-3-carboxamide.

Specific examples of the compounds of the formula (6) are given below.

1-Methylpiperazine,
1-ethylpiperazine,
1-propylpiperazine,
1-isopropylpiperazine,
1-butylpiperazine,
1-isobutylpiperazine,
1-sec-butylpiperazine.

Specific examples of the compounds of the formula (7) are given below.

N-(14-hydroxytetradecyl)-6-(1-piperazinyl)pyridine-3-carboxamide,
N-(15-hydroxypentadecyl)-6-(1-piperazinyl)pyridine-3-carboxamide,
N-(16-hydroxyhexadecyl)-6-(1-piperazinyl)pyridine-3-carboxamide, N-(17-hydroxyheptadecyl)-6-(1-piperazinyl)pyridine-3-carboxamide, N-(18-hydroxyoctadecyl)-6-(1-piperazinyl)pyridine-3-carboxamide.

Specific examples of the compounds of the formula (8) are given below.

6-Chloronicotinic acid, 6-bromonicotinic acid.

Specific examples of the compounds of the formula (9) are given below.

14-Aminotetradecanol, 15-aminopentadecanol, 16-aminohexadecanol, 17-aminoheptadecanol, 18-aminooctadecanol.

Specific examples of the compounds of the formula (10) are given below.

6-Chloronicotinoyl chloride, 6-bromonicotinoyl chloride.

Specific examples of the compounds of the formula (11) are given below.

1,14-Tetradecanediol, 1,15-pentadecanediol, 1,16-hexadecanediol, 1,17-heptadecanediol, 1,18-octadecanediol.

Specific examples of the compounds of the formula (12) are given below.

N-(14-Hydroxytetradecyl)phthalimide,

N-(15-hydroxypentadecyl)phthalimide,

N-(16-hydroxyhexadecyl)phthalimide,

N-(17-hydroxyheptadecyl)phthalimide,

N-(18-hydroxyoctadecyl)phthalimide.

Specific examples of the compounds of the formula (13) are given below.

14-Methoxymethoxytetradecanol, 15-methoxymethoxypentadecanol, 16-methoxymethoxyhexadecanol, 17-methoxymethoxyheptadecanol, 18-methoxymethoxyoctadecanol.

Specific examples of the compounds of the formula (14) are given below.

N-(14-Methoxymethoxytetradecyl)phthalimide,

N-(15-methoxymethoxypentadecyl)phthalimide,

N-(16-methoxymethoxyhexadecyl)phthalimide,

N-(17-methoxymethoxyheptadecyl)phthalimide,

N-(18-methoxymethoxyoctadecyl)phthalimide.

Specific examples of the compounds of the formula (15) are given below.

14-Methoxymethoxytetradecylamine, 15-methoxymethoxypentadecylamine, 16-methoxymethoxyhexadecylamine, 17-methoxymethoxyheptadecylamine, 18-methoxymethoxyoctadecylamine.

Specific examples of the compounds of the formula (16) are given below.

Methyl 14-hydroxytetradecanoate, methyl 15-hydroxypentadecanoate, methyl 16-hydroxyhexadecanoate, methyl 17-hydroxyheptadecanoate, methyl 18-hydroxyoctadecanoate, ethyl 14-hydroxytetradecanoate, ethyl 15-hydroxypentadecanoate, ethyl 16-hydroxyhexadecanoate, ethyl 17-hydroxyheptadecanoate, ethyl 18-hydroxyoctadecanoate.

Specific examples of the compounds of the formula (17) are given below.

Methyl 14-phthalimidotetradecanoate, methyl 15-phthalimidopentadecanoate, methyl 16-phthalimidohexadecanoate, methyl 17-phthalimidoheptadecanoate, methyl 18-phthalimodooctadecanoate, ethyl 14-phthalimidotetradecanoate, ethyl 15-phthalimidopentadecanoate, ethyl 16-phthalimidohexadecanoate, ethyl 17-phthalimidoheptadecanoate, ethyl 18-phthalimodooctadecanoate.

Specific examples of the compounds of the formula (18) are given below.

Methyl 14-aminotetradecanoate, methyl 15-aminopentadecanoate, methyl 16-aminohexadecanoate, methyl 17-aminoheptadecanoate, methyl 18-aminooctadecanoate, ethyl 14-aminotetradecanoate, ethyl 15-aminopentadecanoate, ethyl 16-aminohexadecanoate, ethyl 17-aminoheptadecanoate, ethyl 18-aminooctadecanoate.

Specific examples of the compounds of the formula (19) are given below.

Methyl 14-methoxymethoxytetradecanoate, methyl 15-methoxymethoxypentadecanoate, methyl 16-methoxymethoxyhexadecanoate, methyl 17-methoxymethoxyheptadecanoate, methyl 18-methoxymethoxyoctadecanoate, ethyl 14-methoxymethoxytetradecanoate, ethyl 15-methoxymethoxypentadecanoate, ethyl 16-methoxymethoxyhexadecanoate, ethyl 17-methoxymethoxyheptadecanoate, ethyl 18-methoxymethoxyoctadecanoate.

As the pharmaceutically acceptable salts of the compounds according to this invention, there may be mentioned, for example, hydrochloride, sulfate, nitrate, hydrobromide, phosphate, maleate, fumarate, tartarate, malate, succinate, malonate, propionate, methanesulfonate, benzenesulfonate, p-toluenesulfonate, formate, acetate, trifluoroacetate and the like, and those compounds containing plural acidic functional groups such as carboxyl or the like may be isolated in the form of an inorganic salt with a paired ion such as sodium, potassium, lithium, calcium, magnesium or the like.

A part of the compound represented by the formula (1) according to this invention may be metabolized and converted in vivo to a novel pyridine derivative which is effective in the treatment of cerebrovascular disorders. Main metabolic sites are listed below.

1) N-Oxidation at the 4-position of the piperazine ring and at the 1-position of the pyridine ring.

2) Hydroxylation of the piperazine ring, the pyridine ring and $(CH_2)_n$ and ring cleavage of the piperazine ring incidental to the hydroxylation.

3) Hydroxylation and dealkylation of the alkyl group at the 4-position of the piperazine ring.

4) Hydrolysis of the nitrate and the pyridine carboxamide.

Main metabolites of the pyridinecarboxamides (1) of this invention are recited below.

N-(14-nitroxytetradecyl)-6-(1-piperazinyl)pyridine-3-carboxamide N-oxide,
N-(14-nitroxytetradecyl)-6-(4-methyl-1-piperazinyl)pyridine-3-carboxamide N-oxide,
N-(14-nitroxytetradecyl)-6-(4-ethyl-1-piperazinyl)pyridine-3-carboxamide N-oxide,
N-(14-nitroxytetradecyl)-6-(4-propyl-1-piperazinyl)pyridine-3-carboxamide N-oxide,
N-(14-nitroxytetradecyl)-6-(4-isopropyl-1-piperazinyl)pyridine-3-carboxamide N-oxide,
N-(14-nitroxytetradecyl)-6-(4-butyl-1-piperazinyl)pyridine-3-carboxamide N-oxide,
N-(14-nitroxytetradecyl)-6-(4-isobutyl-1-piperazinyl)pyridine-3-carboxamide N-oxide,
N-(14-nitroxytetradecyl)-6-(4-sec-butyl-1-piperazinyl)pyridine-3-carboxamide N-oxide,
N-(15-nitroxypentadecyl)-6-(1-piperazinyl)pyridine-3-carboxamide N-oxide,
N-(15-nitroxypentadecyl)-6-(4-methyl-1-piperazinyl)pyridine-3-carboxamide N-oxide,
N-(15-nitroxypentadecyl)-6-(4-ethyl-1-piperazinyl)pyridine-3-carboxamide N-oxide,
N-(15-nitroxypentadecyl)-6-(4-propyl-1-piperazinyl)pyridine-3-carboxamide N-oxide,
N-(15-nitroxypentadecyl)-6-(4-isopropyl-1-piperazinyl)pyridine-3-carboxamide N-oxide,
N-(15-nitroxypentadecyl)-6-(4-butyl-1-piperazinyl)pyridine-3-carboxamide N-oxide,
N-(15-nitroxypentadecyl)-6-(4-isobutyl-1-piperazinyl)pyridine-3-carboxamide N-oxide,
N-(15-nitroxypentadecyl)-6-(4-sec-butyl-1-piperazinyl)pyridine-3-carboxamide N-oxide,
N-(16-nitroxyhexadecyl)-6-(1-piperazinyl)pyridine-3-carboxamide N-oxide,
N-(16-nitroxyhexadecyl)-6-(4-methyl-1-piperazinyl)pyridine-3-carboxamide N-oxide,
N-(16-nitroxyhexadecyl)-6-(4-ethyl-1-piperazinyl)pyridine-3-carboxamide N-oxide,
N-(16-nitroxyhexadecyl)-6-(4-propyl-1-piperazinyl)pyridine-3-carboxamide N-oxide,
N-(16-nitroxyhexadecyl)-6-(4-isopropyl-1-piperazinyl)pyridine-3-carboxamide N-oxide,
N-(16-nitroxyhexadecyl)-6-(4-butyl-1-piperazinyl)pyridine-3-carboxamide N- oxide,
N-(16-nitroxyhexadecyl)-6-(4-isobutyl-1-piperazinyl)pyridine-3-carboxamide N-oxide,
N-(16-nitroxyhexadecyl)-6-(4-sec-butyl-1-piperazinyl)pyridine-3-carboxamide N-oxide,
N-(17-nitroxyheptadecyl)-6-(1-piperazinyl)pyridine-3-carboxamide N-oxide,
N-(17-nitroxyheptadecyl)-6-(4-methyl-1-piperazinyl)pyridine-3-carboxamide N-oxide,
N-(17-nitroxyheptadecyl)-6-(4-ethyl-1-piperazinyl)pyridine-3-carboxamide N-oxide,
N-(17-nitroxyheptadecyl)-6-(4-propyl-1-piperazinyl)pyridine-3-carboxamide N-oxide,
N-(17-nitroxyheptadecyl)-6-(4-isopropyl-1-piperazinyl)pyridine-3-carboxamide N-oxide,
N-(17-nitroxyheptadecyl)-6-(4-butyl-1-piperazinyl)pyridine-3-carboxamide N-oxide,
N-(17-nitroxyheptadecyl)-6-(4-isobutyl-1-piperazinyl)pyridine-3-carboxamide N-oxide,
N-(17-nitroxyheptadecyl)-6-(4-sec-butyl-1-piperazinyl)pyridine-3-carboxamide N-oxide,
N-(18-nitroxyoctadecyl)-6-(1-piperazinyl)pyridine-3-carboxamide N-oxide,
N-(18-nitroxyoctadecyl)-6-(4-methyl-1-piperazinyl)pyridine-3-carboxamide N-oxide,
N-(18-nitroxyoctadecyl)-6-(4-ethyl-1-piperazinyl)pyridine-3-carboxamide N-oxide,
N-(18-nitroxyoctadecyl)-6-(4-propyl-1-piperazinyl)pyridine- 3-carboxamide N-oxide,
N-(18-nitroxyoctadecyl)-6-(4-isopropyl-1-piperazinyl)pyridine-3-carboxamide N-oxide,
N-(18-nitroxyoctadecyl)-6-(4-butyl-1-piperazinyl)pyridine-3-carboxamide N-oxide,
N-(18-nitroxyoctadecyl)-6-(4-isobutyl-1-piperazinyl)pyridine-3-carboxamide N-oxide,
N-(18-nitroxyoctadecyl)-6-(4-sec-butyl-1-piperazinyl)pyridine-3-carboxamide N-oxide.

The compounds (1) or pharmaceutically acceptable salts thereof according to this invention may be formulated to dosage forms such as tablets, granules, fine granules, powders, capsules, syrups, elixirs, suspensions, emulsions, injections and the like by incorporating suitable excipients, auxiliary agents, lubricants, antiseptics, disintegrating agents, buffer agents, binding agents, wetting agents, emulsifiers, coloring agents, corringents or flavors, and they may be administered orally or parenterally, preferably via intravenous injection or intravenous instillation.

In preparing a pharmaceutical preparation as drugs for internal use, the conventionally applicable auxiliaries such as lactose, sucrose, sorbitol, mannitol, potato starch, corn starch, cellulose derivatives, gelatin and the like are suitable as a carrier and lubricants such as magnesium stearate, Carbowax, polyethylene glycol and the like may be further added. The active compound in admixture with the above may be formed into granules, tablets, capsules and the like according to a conventional method.

In preparing a pharmaceutical preparation in the form of an aqueous preparation, the active ingredient may be dissolved in distilled water for injection and, if necessary, antioxidants, stabilizers, solubilizing agents, water-soluble surfactants, non-aqueous solvents, buffer agents, pH adjusters, preservatives, isotonic agents or soothing agents may be added and the resultant aqueous solution may be filtered, filled and sealed in a conventional manner and then sterilized by means of autoclaved sterilization or hot air sterilization to prepare injections.

In preparing a pharmaceutical preparation in the form of an emulsifiable injection, the sterilized active ingredient may be dissolved in a non-aqueous solvent and, if necessary, distilled water for injection, antioxidants, stabilizers, solubilizing agents, water-soluble surfactants, buffer agents, pH adjusters, preservatives, isotonic agents or soothing agents may be added and then the resultant emulsion may be filtered, filled and sealed in a conventional manner to prepare injections.

A dose of the compound or pharmaceutically acceptable salt thereof according to this invention may be selected depending upon the body weight, age, sex, lapsed time after onset, classification of diseases and others, and it is 1–1000 mg per day.

BEST MODE FOR CARRYING OUT THE INVENTION

This invention will be more specifically illustrated by way of the following Preparation Examples, Pharmacological Effect and Formulation Examples, but this invention is not intended to be limited thereto.

EXAMPLE 1

N-(14-Nitroxytetradecyl)-6-(4-methyl-1-piperazinyl)pyridine-3-carboxamide

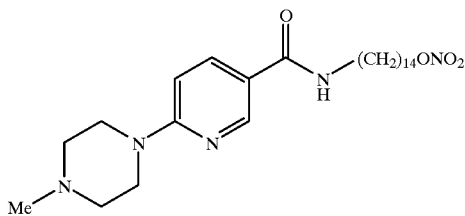

To 5 ml of fuming nitric acid cooled to −10° C. was gradually added 0.5 g of N-(14-hydroxytetradecyl)-6-(4-methyl-1-piperazinyl)pyridine-3-carboxamide and the mixture was stirred for 30 minutes. The reaction solution was poured into water, neutralized with sodium hydrogen carbonate and extracted with chloroform. The extract was dried over anhydrous sodium sulfate and distilled under reduced pressure. The residue thus obtained was chromatographed over silica gel column to afford the title compound as a colorless crystal.

mp 82–83° C.

$^1$H NMR (CDCl$_3$) δ 1.25–1.40 (m, 20H), 1.59 (quint, 2H), 1.71 (quint, J=6.8 Hz, 2H), 2.34 (s, 3H), 2.50 (t, J=4.8 Hz, 4H), 3.42 (t, J=6.8 Hz, 2H), 3.66 (t, J=4.8 Hz, 4H), 4.44 (t, J=6.8 Hz, 2H), 5.92 (brs, 1H), 6.62 (d, J=9.2 Hz, 1H), 7.90 (dd, J=2.4, 9.2 Hz, 1H), 8.53 (d, J=2.4 Hz, 1H)

EXAMPLE 2

N-(14-Nitroxytetradecyl)-6-(4-methyl-1-piperazinyl)pyridine-3-carboxamide

EXAMPLE 2-1

N-(14-Aminotetradecyl nitrate

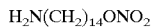

To fumic nitric acid (25 ml) cooled to −30° C. was added crystals of 14-aminotetradecanol (8.48 g) while stirring for 30 minutes. The mixture was stirred below −20° C. for a further 30 minutes, poured into ice-water, neutralized with sodium hydrogen carbonate and extracted with chloroform. The separated organic layer was distilled off under reduced pressure to afford the title compound as an oily substance. This product was provided for the subsequent reaction without purification.

EXAMPLE 2-2

N-(14-Nitroxytetradecyl)-6-(4-methyl-1-piperazinyl)pyridine-3-carboxamide

To sodium 6-(4-methylpiperazinyl)pyridine-3-carboxylate and 14-aminotetradecyl nitrate was added 150 ml of methylene chloride and then 6.80 g of 1-ethyl-3-(3-dimethylaminopropyl)carbodiimide hydrochloride (WSCI) and 5.00 g of 1-hydroxybenzotriazole (HOBt) were added at room temperature while stirring and then the mixture was stirred at room temperature for 15 hours. The reaction solution was chromatographed over a silica gel column and the residue was purified by recrystallization to afford the title compound as a colorless crystal.

EXAMPLE 3

N-(14-Nitroxytetradecyl)-6-(4-methyl-1-piperazinyl)pyridine-3-carboxamide

EXAMPLE 3-1

N-(14-Iodotetradecyl)-6-(4-methyl-1-piperazinyl)pyridine-3-carboxamide

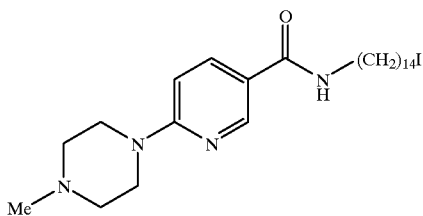

A solution of N-(14-hydroxytetradecyl)-6-(4-methyl-1-piperazinyl)pyridine-3-carboxamide in 57% hydriodic acid was stirred at 120° C. for 30 minutes. The reaction solution was diluted with water and extracted with chloroform. The chloroform layer was washed successively with a saturated aqueous solution of sodium hydrogen carbonate and a saturated aqueous solution of sodium chloride and then dried over anhydrous magnesium sulfate. The solvent was distilled off under reduced pressure to afford the title compound.

EXAMPLE 3-2

N-(14-Nitroxytetradecyl)-6-(4-methyl-1-piperazinyl)pyridine-3-carboxamide

To a solution of N-(14-iodotetradecyl)-6-(4-methyl-1-piperazinyl)pyridine-3-carboxamide in toluene-acetonitrile was added silver nitrate and the mixture was stirred at 35° C. for 3.5 hours. The reaction solution was filtered and then water and chloroform were added and the mixture was washed with a saturated aqueous solution of sodium chloride. The organic layer was dried over anhydrous magnesium sulfate and distilled off. The residue thus obtained was chromatographed over a silica gel column to afford the title compound.

EXAMPLE 4

N-(14-Nitroxytetradecyl)-6-(4-methyl-1-piperazinyl)pyridine-3-carboxamide

EXAMPLE 4-1

N-(14-Mesyloxytetradecyl)-6-(4-methyl-1-piperazinyl)pyridine-3-carboxamide

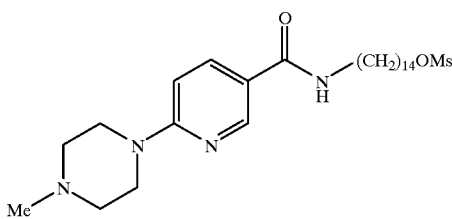

To a solution of N-(14-hydroxytetradecyl)-6-(4-methyl-1-piperazinyl)pyridine-3-carboxamide in chloroform were added triethylamine, pyridine and methanesulfonyl chloride and the mixture was stirred at room temperature for 30 minutes. The reaction solution was washed successively with water, 3N-hydrochloric acid and a saturated aqueous solution of sodium chloride and dried over anhydrous magnesium sulfate. The solvent was distilled off under reduced pressure and the residue thus obtained was chromatographed over a silica gel column to afford the title compound.

EXAMPLE 4-2

Preparation of Amberlyst A-26( manufactured by Rohm & Haas Co.) of a nitrate form 50 g of Amberlyst A-26 (Cl form) was washed successively with 300 ml each of methanol, water and a 2.5N aqueous solution of sodium hydroxide and 350 ml of ion exchanged water and then converted to the nitrate form with 300 ml of 1N-nitric acid. After conversion, it was washed with ion exchanged water until it became neutral and then replaced with 200 ml of ethanol and 100 ml of acetone. The Amberlyst A-26 (a nitrate form) thus obtained was dried at 50° C. under reduced pressure for 2 hours.

EXAMPLE 4-3

N-(14-Nitroxytetradecyl)-6-(4-methyl-1-piperazinyl) pyridine-3-carboxamide

To a solution of N-(14-mesyloxytetradecyl)-6-(4-methyl-1-piperazinyl)pyridine-3-carboxamide in toluene was added Amberlyst A-26 (a nitrate form) and the mixture was heated under reflux for 3 hours. The ion-exchange resin was filtered off and the filtrate was distilled off. The residue thus obtained was chromatographed over a silica gel column to afford 0.85 g of the title compound.

EXAMPLE 5

N-(14-Nitroxytetradecyl)-6-(4-ethyl-1-piperazinyl) pyridine-3-carboxamide

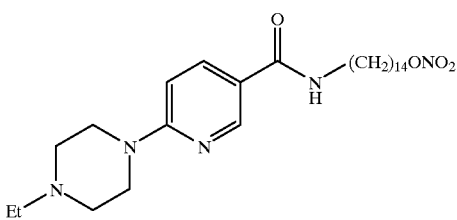

Synthesis was carried out in the same manner as described in Example 1 using as a starting material N-(14-hydroxytetradecyl)-6-(4-ethyl-1-piperazinyl)pyridine-3-carboxamide to afford the title compound.

$^1$H NMR (CDCl$_3$) δ 1.13 (t, J=7 Hz, 3H), 1.21–1.44 (m, 20H), 1.59 (quint, J=7 Hz, 2H), 1.72 (quint, J=7 Hz, 2H), 2.47 (q, J=7 Hz, 2H), 2.54 (t, J=5 Hz, 4H), 3.42 (q, J=7 Hz, 2H), 3.67 (t, J=5 Hz, 4H), 4.44 (t, J=7 Hz, 2H), 5.86–5.94 (brm, 1H), 6.63 (d, J=9 Hz, 1H), 7.90 (dd, J=2, 9 Hz, 1H), 8.53 (d, J=2 Hz, 1H)

EXAMPLE 6

N-(14-Nitroxytetradecyl)-6-(1-piperazinyl)pyridine-3-carboxamide

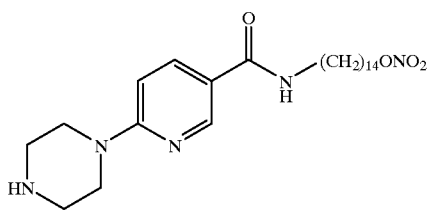

Synthesis was carried out in the same manner as described in Example 1 using as a starting material N-(14-hydroxytetradecyl)-6-(1-piperazinyl)-pyridine-3-carboxamide to afford the title compound.

$^1$H NMR (CDCl$_3$) δ 1.18–1.44 (m, 20H), 1.60 (quint, J=7 Hz, 2H), 1.72 (quint, J=7 Hz, 2H), 1.76–2.04 (b, 1H), 3.02 (t, J=5 Hz, 4H), 3.43 (q, J=7 Hz, 2H), 3.66 (t, J=5 Hz, 4H), 4.44 (t, J=7 Hz, 2H), 5.87–5.96 (brs, 1H), 6.63 (d, J=9 Hz, 1H), 7.91 (dd, J=2, 9 Hz, 1H), 8.54 (d, J=2 Hz, 1H)

EXAMPLE 7

N-(14-Nitroxytetradecyl)-6-(4-propyl-1-piperazinyl) pyridine-3-carboxamide

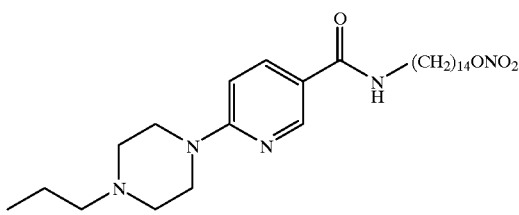

Synthesis was carried out in the same manner as described in Example 1 using as a starting material N-(14-hydroxytetradecyl)-6-(4-propyl-1-piperazinyl)pyridine-3-carboxamide to afford the title compound.

$^1$H NMR (CDCl$_3$) δ 0.93 (t, J=7 Hz, 3H), 1.18–1.44 (m, 20H), 1.49–1.67 (m, 4H), 1.72 (quint, J=7 Hz, 2H), 2.35 (t, J=7 Hz, 2H), 2.54 (t, J=5 Hz, 4H), 3.42 (q, J=7 Hz, 2H), 3.66 (t, J=5 Hz, 4H), 4.44 (t, J=7 Hz, 2H), 5.86–5.95 (bm, 1H), 6.62 (d, J=9 Hz, 1H), 7.90 (dd, J=2,9 Hz, 1H), 8.53 (d, J=2 Hz, 1H)

EXAMPLE 8

N-(14-Nitroxytetradecyl)-6-(4-isopropyl-1-piperazinyl) pyridine-3-carboxamide

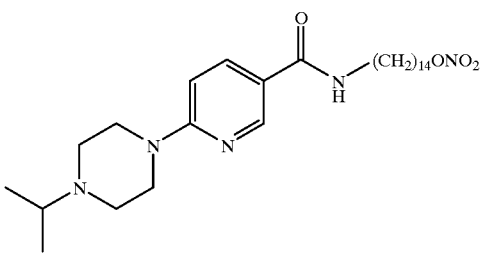

Synthesis was carried out in the same manner as described in Example 1 using as a starting material N-(14-hydroxytetradecyl)-6-(4-isopropyl-1-piperazinyl)pyridine-3-carboxamide to afford the title compound.

$^1$H NMR (CDCl$_3$) δ 1.09 (d, J=7 Hz, 6H), 1.20–1.42 (m, 20H), 1.55–1.62 (m, 2H), 1.72 (quint, J=7 Hz, 2H), 2.56–2.68 (m, 4H), 2.68–2.81 (m, 1H), 3.42 (q, J=7 Hz, 2H), 3.61–3.70 (m, 4H), 4.44 (t, J=7 Hz, 2H), 5.84–5.96 (bm, 1H), 6.62 (d, J=9 Hz, 1H), 7.89 (dd, J=2, 9 Hz, 1H), 8.53 (d, J=2 Hz, 1H)

EXAMPLE 9

N-(16-Nitroxyhexadecyl)-6-(4-methyl-1-piperazinyl)pyridine-3-carboxamide

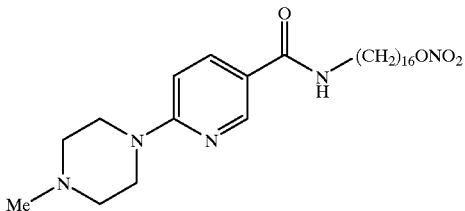

Synthesis was carried out in the same manner as described in Example 1 using as a starting material N-(16-hydroxyhexadecyl)-6-(4-methyl-1-piperazinyl)pyridine-3-carboxamide to afford the title compound as a colorless crystal.

mp 85–87.5° C.

$^1$H NMR (CDCl$_3$) δ 1.23–1.41 (m, 24H), 1.55–1.62 (m, 2H), 1.67–1.75 (m, 2H), 2.34 (s, 3H), 2.50 (t, J=4.8 Hz, 4H), 3.42 (q, J=6.8 Hz), 3.66 (t, J=4.8 Hz, 4H), 4.44 (t, J=6.8 Hz, 2H), 5.91 (brs, 1H), 6.62 (d, J=9.2 Hz, 1H), 7.90 (dd, J=2.9, 9.2 Hz, 1H), 8.53 (d, J=2.9 Hz, 1H)

EXAMPLE 10

N-(16-Nitroxyhexadecyl)-6-(4-ethyl-1-piperazinyl)pyridine-3-carboxamide

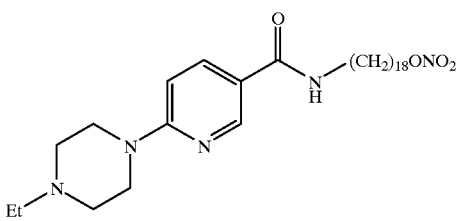

Synthesis was carried out in the same manner as described in Example 1 using as a starting material N-(16-hydroxyhexadecyl)-6-(4-ethyl-1-piperazinyl)pyridine-3-carboxamide to afford the title compound as a colorless crystal.

$^1$H NMR (CDCl$_3$) δ 1.13 (t, J=7 Hz, 3H), 1.21–1.44 (m, 24H), 1.49–1.65 (m, 2H), 1.71 (quint, J=7 Hz, 2H), 2.47 (q, J=7 Hz, 2H), 2.55 (t, J=5 Hz, 4H), 3.42 (q, J=7 Hz, 2H), 3.68 (t, J=5 Hz, 4H), 4.44 (t, J=7 Hz, 2H), 5.85– 5.93 (bm, 1H), 6.63 (d, J=9 Hz, 1H), 7.90 (dd, J=2 Hz, 9 Hz, 1H), 8.53 (d, J=2 Hz, 1H)

EXAMPLE 11

N-(16-Nitroxyhexadecyl)-6-(4-isopropyl-1-piperazinyl)pyridine-3-carboxamide

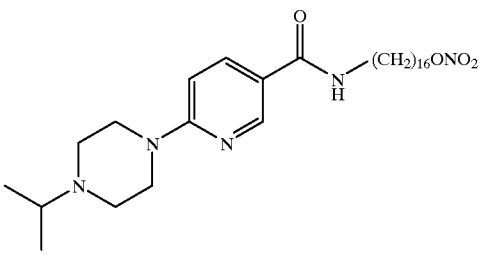

Synthesis was carried out in the same manner as described in Example 1 using as a starting material N-(16-hydroxyhexadecyl)-6-(4-isopropyl-1-piperazinyl)pyridine-3-carboxamide to afford the title compound as a colorless crystal.

$^1$H NMR (CDCl$_3$) δ 1.08 (d, J=6 Hz, 6H), 1.18–1.44 (m, 24H), 1.49–1.65 (m, 2H), 1.72 (quint, J=7 Hz, 2H), 2.56–2.67 (m, 4H), 2.67–2.81 (m, 1H), 3.42 (q, J=7 Hz, 2H), 3.60–3.71 (m, 4H), 4.44 (t, J=7 Hz, 2H), 5.85–5.93 (bm, 1H), 6.62 (d, J=9 Hz, 1H), 7.89 (dd, J=2 Hz, 9 Hz, 1H), 8.53 (d, J=2 Hz, 1H)

EXAMPLE 12

N-(16-Nitroxyhexadecyl)-6-(1-piperazinyl)pyridine-3-carboxamide

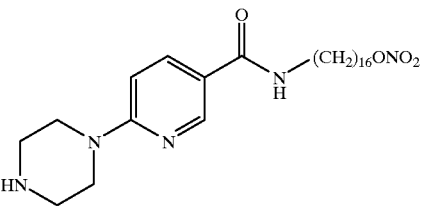

Synthesis was carried out in the same manner as described in Example 1 using as a starting material N-(16-hydroxyhexadecyl)-6-(1-piperazinyl)pyridine-3-carboxamide to afford the title compound.

$^1$H NMR (CDCl$_3$) δ 1.25–1.50 (m, 24H), 1.59–1.67 (m, 2H), 1.72 (quint, J=7 Hz, 2H), 2.98 (t, J=5 Hz, 4H), 3.42 (q, J=7 Hz, 2H), 3.62 (t, J 5 Hz, 4H), 4.44 (t, J=7 Hz, 2H), 5.83–5.96 (brm, 1H), 6.62 (d, J=9 Hz, 1H), 7.90 (dd, J=2, 9 Hz, 1H), 8.53 (d, J=2 Hz, 1H)

EXAMPLE 13

N-(18-Nitroxyoctadecyl)-6-(4-methyl-1-piperazinyl)pyridine-3-carboxamide

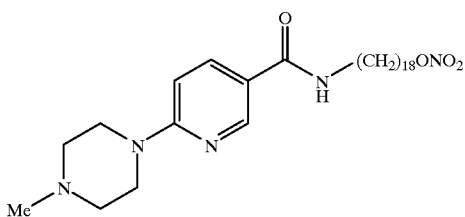

Synthesis was carried out in the same manner as described in Example 1 using as a starting material N-(18-hydroxyoctadecyl)-6-(4-methyl-1-piperazinyl)pyridine-3-carboxamide to afford the title compound as a colorless crystal.

mp 88.5–89.5° C.

$^1$H NMR (CDCl$_3$) δ 1.22–1.41 (m, 28H), 1.59 (quint, J=7.3 Hz, 2H), 1.67–1.75 (m, 2H), 2.34 (s, 3H), 2.51 (t, J=4.8 Hz, 4H), 3.42 (q, J=7.3 Hz, 2H), 3.66 (t, J=4.8 Hz, 4H), 4.44 (t, J=6.8 Hz, 2H), 5.90 (brs, 1H), 6.62 (d, J=8.7 Hz, 1H), 7.90 (dd, J=2.4, 8.7 Hz, 1H), 8.53 (d, J=2.4 Hz, 1H)

EXAMPLE 14

N-(18-Nitroxyoctadecyl)-6-(1-piperazinyl)pyridine-3-carboxamide

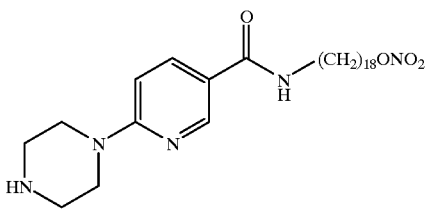

Synthesis was carried out in the same manner as described in Example 1 using as a starting material N-(18-hydroxyoctadecyl)-6-(1-piperazinyl)pyridine-3-carboxamide to afford the title compound as colorless crystal.

$^1$H NMR (CDCl$_3$) δ 1.18–1.44 (m, 28H), 1.60 (quint, J=7 Hz, 2H), 1.71 (quint, J=7 Hz, 2H), 3.00 (t, J=5 Hz, 4H), 3.43 (q, J=7 Hz, 2H), 3.64 (t, J=5 Hz, 4H), 4.44 (t, J=7 Hz, 2H), 5.86–5.96 (b, 1H), 6.62(d, J=9 Hz, 1H), 7.91 (dd, J=2 Hz, 9 Hz, 1H), 8.53 (d, J=2 Hz, 1H)

PREPARATION EXAMPLE 1

N-(14-Hydroxytetradecyl)-6-(4-methyl--piperazinyl)pyridine-3-carboxamide

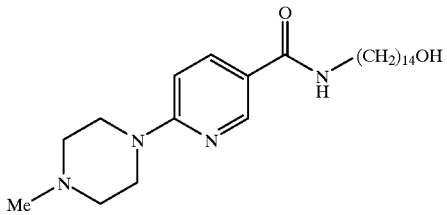

To 1.0 g of N-(14-hydroxytetradecyl)-6-chloropyridine-3-carboxamide was added 5 ml of 1-methylpiperazine and the mixture was heated at 160° C. for 30 minutes. The reaction solution was diluted with chloroform and washed with water, dried over anhydrous sodium sulfate and then distilled off under reduced pressure. The residue thus obtained was chromatographed over a silica gel column to afford the title compound as crystals.

mp 118.5–120° C.

$^1$H NMR (CDCl$_3$) δ 1.25–1.32 (m, 20H), 1.53–1.61 (m, 4H), 2.34 (s,3H), 2.51 (t, J=4.8 Hz, 4H), 3.39–3.44 (m, 2H), 3.62–3.67 (m, 6H), 5.91 (brs, 1H), 6.62 (d, J=9.2 Hz, 1H), 7.90 (dd, J=2.4, 9.2 Hz, 1H), 8.52 (d, J=2.4 Hz, 1H).

PREPARATION EXAMPLE 2

N-(14-Hydroxytetradecyl)-6-chloropyridine-3-carboxamide

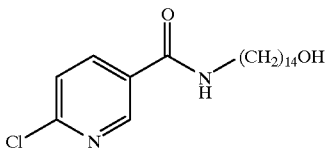

To a suspension of 1.0 g of 14-aminotetradecanol and 0.68 g of 6-chloronicotinic acid in 20 ml of dichloromethane was added 0.83 g of 1-ethyl-3-(3-dimethylaminopropyl)carbodiimide hydrochloride (WSCl) and then the mixture was stirred overnight. The precipitate was recovered by filtration with chloroform and washed with water to afford the title compound as a colorless crystal. The crystal thus obtained was used for the subsequent reaction without purification.

PREPARATION EXAMPLE 3

N-(14-Hydroxytetradecyl)-6-(4-ethyl-1-piperazinyl)pyridine-3-carboxamide

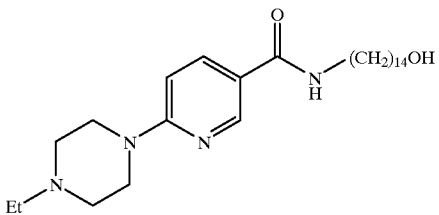

Synthesis was carried out in the same manner as described in Preparation Example 1 using as a starting material N-(14-hydroxytetradecyl)-6-chloropyridine-3-carboxamide and 1-ethylpiperazine to afford the title compound as a crystal. The crystal thus obtained was used for the subsequent reaction without purification.

PREPARATION EXAMPLE 4

N-(14-Hydroxytetradecyl)-6-(1-piperazinyl)pyridine-3-carboxamide

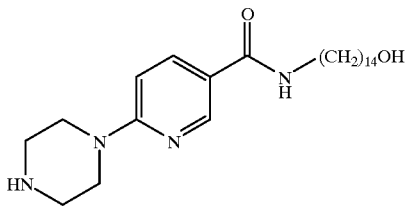

To a suspension of 2.50 g of N-(14-hydroxytetradecyl)-6-chloropyridine-3-carboxamide in 50 ml of toluene was added 3.0 g of piperazine and the mixture was heated under reflux for 10 hours. Then, the reaction solution was distilled under reduced pressure. The crystal thus obtained was used for the subsequent reaction without purification.

PREPARATION EXAMPLE 5

N-(14-Hydroxytetradecyl)-6-(4-propyl-1-piperazinyl)pyridine-3-carboxamide

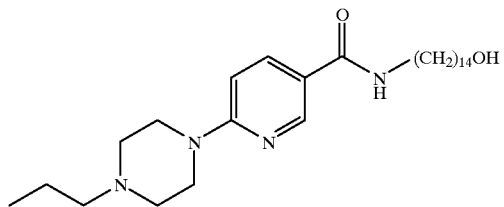

A solution of N-(14-hydroxytetradecyl)-6-(1-piperazinyl)pyridine-3-carboxamide, 1-bromopropane and potassium carbonate in dimethylformamide was heated at 100° C. for 3 hours. The reaction solution was diluted with chloroform and washed successively with water and a saturated aqueous solution of sodium chloride. It was dried over anhydrous sodium sulfate and the solvent was distilled off under reduced pressure. The residue thus obtained was chromatographed over a silica gel column to afford the title compound as a crystal. The crystal thus obtained was used for the subsequent reaction without purification.

PREPARATION EXAMPLE 6

N-(14-Hydroxytetradecyl)-6-(4-isopropyl-1-piperazinyl)pyridine-3-carboxamide

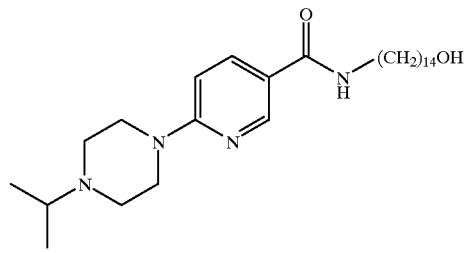

Synthesis was carried out in the same manner as described in Preparation Example 5 using as a starting material N-(14-hydroxytetradecyl)-6-(1-piperazinyl)pyridine-3-carboxamide and 2-bromopropane to afford the title compound as a crystal. The crystal thus obtained was used for the subsequent reaction without purification.

PREPARATION EXAMPLE 7

N-(16-Hydroxyhexadecyl)-6-chloropyridine-3-carboxamide

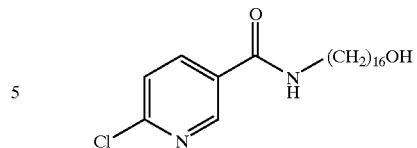

Synthesis was carried out in the same manner as described in Preparation Example 2 using as starting materials 16-aminohexadecanol and 6-chloronicotinic acid to afford the title compound as a colorless crystal. The crystal thus obtained was used for the subsequent reaction without purification.

PREPARATION EXAMPLE 18

N-(16-Hydroxyhexadecyl)-6-(4-methyl-1-piperazinyl)pyridine-3-carboxamide

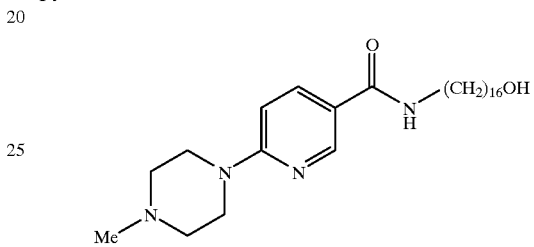

Synthesis was carried out in the same manner as described in Preparation Example 1 using as starting materials N-(16-hydroxyhexadecyl)-6-chloropyridine-3-carboxamide and 1-methylpiperazine to afford the title compound as a crystal.

$^1$H NMR (CDCl$_3$) δ 1.23–1.38 (m, 24H), 1.53–1.62 (m, 4H), 2.34 (s,3H), 2.50 (t, J=4.8 Hz, 4H), 3.42 (q, J=6.8 Hz, 2H), 3.62–3.67 (m,6H), 5.94 (brs, 1H), 6.62 (d, J=8.7 Hz, 1H), 7.90 (dd, J=2.4, 8.7 Hz, 1H), 8.53 (d, J=2.4 Hz, 1H)

PREPARATION EXAMPLE 9

N-(16-Hydroxyhexadecyl)-6-(4-ethyl-1-piperazinyl)pyridine-3-carboxamide

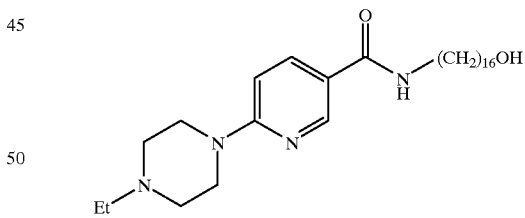

Synthesis was carried out in the same manner as described in Preparation Example 1 using as starting materials N-(16-hydroxyhexadecyl)-6-chloropyridine-3-carboxamide and 1-ethylpiperazine to afford the title compound as a crystal.

$^1$H NMR (CDCl$_3$) δ 1.13 (t, J=7 Hz, 3H), 1.19–1.41 (m, 24H), 1.50–1.64 (m, 4H), 2.46 (q, J=7 Hz, 2H), 2.54 (t, J=5 Hz, 4H), 3.42 (q, J=7 Hz, 2H), 3.64 (t, J=7 Hz, 2H), 3.67 (t, J=5 Hz, 4H), 5.86–5.95 (bm,1H), 6.63 (d, J=9 Hz, 1H), 7.90 (dd, J=2 Hz, 9 Hz, 1H), 8.53 (d, J=2 Hz, 1H)

PREPARATION EXAMPLE 10

N-(16-Hydroxyhexadecyl)-6-(4-isopropyl-1-piperazinyl)pyridine-3-carboxamide

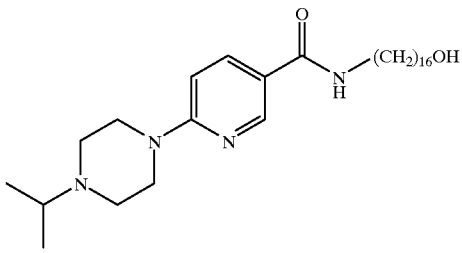

Synthesis was carried out in the same manner as described in Preparation Example 1 using as starting materials N-(16-hydroxyhexadecyl)-6-chloropyridine-3-carboxamide and 1-isopropylpiperazine to afford the title compound as a crystal.

¹H NMR (CDCl₃) δ 1.08 (d, J=6 Hz, 6H), 1.19–1.45 (m, 24H), 1.49–1.69 (m, 4H), 2.62 (t, J=5 Hz, 4H), 2.73 (sept, J=6 Hz, 1H), 3.42 (q,J=7 Hz, 2H), 3.57–3.73 (m, 6H), 5.91 (bt, J=6 Hz, 1H), 6.62 (d, J=9 Hz, 1H), 7.89 (dd, J=2 Hz, 9 Hz, 1H), 8.53 (d, J=2 Hz, 1H)

PREPARATION EXAMPLE 11

N-(16-Hydroxyhexadecyl)-6-(1-piperazinyl)pyridine-3-carboxamide

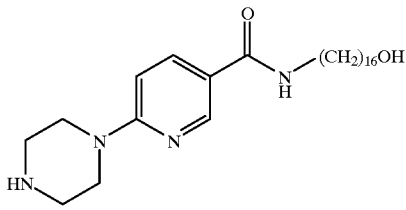

To a suspension of N-(16-hydroxyhexadecyl)-6-chloropyridine-3-carboxamide in toluene was added piperazine and the mixture was heated under reflux for 10 hours. Then, the reaction solution was distilled off under reduced pressure. The residue was chromatographed over a silica gel column to afford the title compound as a crystal.

PREPARATION EXAMPLE 12

N-(18-Hydroxyoctadecyl)-6-chloropyridine-3-carboxamide

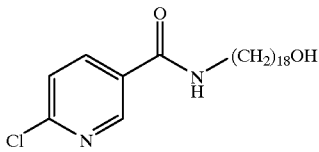

Synthesis was carried out in the same manner as described in Preparation Example 2 using as starting materials 18-aminooctadecanol and 6-chloronicotinic acid to afford the title compound as a crystal.

¹H NMR (CDCl₃) δ 1.13–1.39 (m, 28H), 1.55–1.66 (m, 4H), 3.46 (q, J=7.3 Hz, 2H), 3.64 (t, J=6.8 Hz, 2H), 6.08 (brs, 1H), 7.41 (d, J=8.3 Hz, 1H), 8.07 (dd, J=2.4, 8.3 Hz, 1H), 8.71 (d, J=2.4 Hz, 1H)

PREPARATION EXAMPLE 13

N-(18-Hydroxyoctadecyl)-6-(4-methyl-1-piperazinyl)pyridine-3-carboxamide

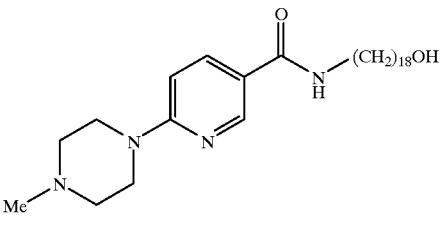

Synthesis was carried out in the same manner as described in Preparation Example 1 using as starting materials N-(18-hydroxyoctadecyl)-6-chloropyridine-3-carboxamide and 1-methylpiperazine to afford the title compound as a crystal.

¹H NMR (CDCl₃) δ 1.23–1.38 (m, 28H), 1.54–1.62 (m, 4H), 2.35 (s, 3H), 2.51 (t, J=4.8 Hz, 4H), 3.42 (q, J=6.8 Hz, 2H), 3.63 (t, J=6.8 Hz, 2H), 3.66 (t, J=4.8 Hz, 4H), 6.91 (brs, 1H), 6.62 (d, J=8.7 Hz, 1H), 7.90 (dd, J=2.4, 8.7 Hz, 1H), 8.52 (d, J=2.4 Hz, 1H)

PREPARATION EXAMPLE 14

N-(18-Hydroxyoctadecyl)-6-(1-piperazinyl)pyridine-3-carboxamide

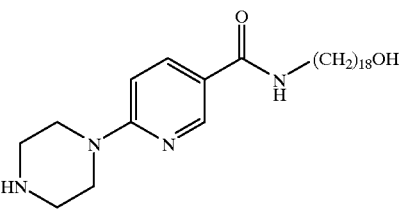

To a suspension of 2.00 g of N-(18-hydroxyoctadecyl)-6-chloropyridine-3-carboxamide in 60 ml of toluene was added 4.00 g of piperazine and the mixture was heated under reflux for 5 hours. Then, it was allowed to stand over 3 nights. The crystal thus precipitated out was dispersed in water and recovered by filtration. After washing with water, the crystal was dried under reduced pressure to afford a crude crystal of the title compound. It was dissolved in hot chloroform and insolubles were filtered off. The filtrate was distilled off at ordinary pressure, hexane was added, the crystal thus precipitated out was recovered by filtration and then dried under reduced pressure to afford 1.47 g of the title compound as a crystal.

¹H NMR (CDCl₃) δ 1.18–1.42 (28H, m, 14×CH2), 1.47–1.65 (4H, m,2×CH2), 2.97 (4H, t, J=5 Hz, Piperaz 3, 5-H), 3.42 (2H, q, J=7 Hz, 1-CH2), 3.61 (4H, t, J=5 Hz, Piperaz 2, 6 - H), 3.64 (2H, t, J=7 Hz, 18 - CH2), 5.86–5.95 (1H, b, CONH), 6.62 (1H, d, J=9 Hz, Py 5 - H), 7.90 (1H, dd, J=2 Hz, 9 Hz, Py 4 - H), 8.53 (1H, d, J=2 Hz, Py 2 - H)

PREPARATION EXAMPLE 15

Diethyl tetradecanedioate

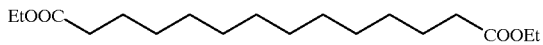

To a solution of 5.0 g of tetradecanedioic acid in 100 ml of ethanol was added 0.2 ml of sulfuric acid and the mixture was heated under reflux for one hour. The reaction solution was distilled under reduced pressure and the residue was diluted with ethyl acetate and washed successively with water, a saturated aqueous solution of sodium hydrogen carbonate and a saturated aqueous solution of sodium chloride and dried over anhydrous sodium sulfate to afford the title compound as a pale yellow oily substance.

$^1$H NMR (CDCl$_3$) δ 1.23–1.28 (m, 22H), 1.59–1.63 (m, 4H), 2.38 (t,J=7.8 Hz, 4H), 4.12 (q, J=7.3 Hz, 4H)

PREPARATION EXAMPLE 16

1,14-Tetradecanediol

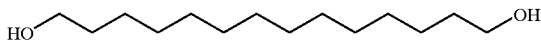

To a solution of 6.0 g of diethyl tetradecanedioate in 80 ml of tetrahydrofuran was added 1.5 g of lithium aluminum hydride and the mixture was stirred for one hour. After addition of a saturated aqueous solution of sodium sulfate, the insolubles thus precipitated out was filtered off and the filtrate was distilled under reduced pressure to afford the title compound.

$^1$H NMR (CD$_3$OD) δ 1.30–1.38 (m, 20H), 1.48–1.53 (m, 4H), 3.52 (t, J=6.8 Hz, 4H)

PREPARATION EXAMPLE 17

N-(14-Hydroxytetradecyl)phthalimide

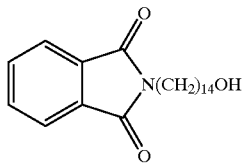

To a suspension of 4.0 g of 1,14-tetradecanediol, 4.56 g of triphenylphosphine and 2.25 g of phthalimide in 150 ml of tetrahydrofuran was added dropwise at 0° C. a solution of 7.59 ml of diethyl azodicarboxylate (40%/toluene) in 10 ml of tetrahydrofuran and the mixture was stirred at room temperature overnight. The reaction solution was distilled under reduced pressure, diethyl ether was added to the residue and the precipitate thus separated was filtered off. The filtrate was distilled under reduced pressure and chromatographed over a silica gel column to afford the title compound as a crystal. The crystal thus obtained was used for the subsequent reaction without purification.

PREPARATION EXAMPLE 18

N-(14-Hydroxytetradecyl)phthalimide

To 19.5 g of 1,14-tetradecanediol were added 200 ml of toluene and 29.5 ml of 48% hydrobromic acid and the mixture was heated under reflux for 2 hours. After completion of the reaction, the reaction solution was washed with an aqueous solution of sodium hydrogen carbonate and the solvent was distilled off.

The reaction solution was distilled and to the residue thus obtained were added 30 g of potassium phthalimide and 200 ml of DMF and the mixture was allowed to react at 100° C. for 3 hours. After the reaction solution was distilled, the residue was chromatographed over silica gel column to afford the title compound as a colorless crystal.

PREPARATION EXAMPLE 19

14-Aminotetradecanol

To a suspension of N-(14-hydroxytetradecyl)phthalimide in 100 ml of methanol was added 0.87 g of hydrazine monohydrate and the mixture was heated under reflux for 3 hours. The reaction solution was distilled under reduced pressure and the residue was diluted with a 1N aqueous solution of sodium hydroxide and then extracted twice with chloroform. The organic layers were combined, washed with a saturated aqueous solution of sodium chloride, dried over anhydrous sodium sulfate and then distilled under reduced pressure. Chromatography over silica gel afforded the title compound as a colorless crystal.

PREPARATION EXAMPLE 20

Ethyl 16-hydroxyhexadecanoate

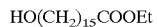

To a solution of 5.0 g of 16-hydroxyhexadecanoic acid in 100 ml of ethanol was added 0.2 ml of sulfuric acid and the mixture was heated under reflux for one hour. The reaction solution was distilled off under reduced pressure. The residue was diluted with ethyl acetate and washed successively with water, a saturated aqueous solution of sodium hydrogen carbonate and a saturated aqueous solution of sodium chloride, dried over anhydrous sodium sulfate and then distilled under reduced pressure to afford the title compound.

$^1$H NMR (CDCl$_3$) δ 1.23–1.27 (m, 27H), 1.54–1.61 (m, 2H), 2.28 (t, J=7.3 Hz, 2H), 3.64 (t, J=6.3 Hz, 2H), 4.12 (q, J=7.3 Hz, 2H)

PREPARATION EXAMPLE 21

Ethyl 16-methoxymethoxyhexadecanoate

MOMO(CH$_2$)$_{15}$COOEt

To a solution of 5.44 g of ethyl 16-hydroxyhexadecanoate in 80 ml of dichloromethane was added under ice-cooling 1.63 ml of methoxymethyl chloride, 4.1 ml of diisopropylethylamine was added dropwise and then the mixture was stirred overnight. The reaction solution was diluted with chloroform, washed with water, dried over anhydrous sodium sulfate and distilled under reduced pressure. The residue was chromatographed over a silica gel column to afford the title compound as a colorless oily substance.

$^1$H NMR (CDCl$_3$) δ 1.23–1.27 (m, 27H), 1.55–1.63 (m, 2H), 2.28 (t, J=7.3 Hz, 2H), 3.36 (s, 3H), 3.51 (t, J=6.8 Hz, 2H), 4.12 (q, J=7.3 Hz, 2H), 4.62 (s, 2H)

PREPARATION EXAMPLE 22

16-Methoxymethoxyhexadecanol

To a solution of 3.0 g of ethyl 16-methoxymethoxyhexadecanoate in 50 ml of tetrahydrofuran was added under ice-cooling 1.5 g of lithium aluminum hydride and the mixture was stirred for one hour. After a saturated aqueous solution of sodium sulfate was added, the insolubles precipitated out were filtered off and distilled under reduced pressure. The residue was chromatographed over a silica gel column to afford the title compound as a colorless oily substance.

$^1$H NMR (CDCl$_3$) δ 1.23–1.36 (m, 24H), 1.53–1.62 (m, 4H), 3.36 (s, 3H), 3.51 (t, J=6.8 Hz, 2H), 3.63–3.64 (m, 2H), 4.62 (s, 2H)

PREPARATION EXAMPLE 23

N-(16-Methoxymethoxyhexadecyl)phthalimide

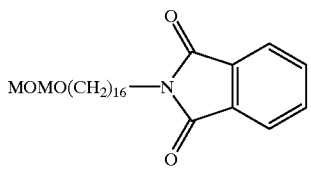

To a solution of 1.0 g of 16-methoxymethoxyhexadecanol, 0.86 g of triphenylphosphine and 0.48 g of phthalimide in 25 ml of tetrahydrofuran was added dropwise under ice-cooling a solution of diethyl azodicarboxylate in 5 ml of tetrahydrofuran and the mixture was stirred overnight. The reaction solution was distilled under reduced pressure and chromatographed over a silica gel column to afford the title compound as a colorless crystal.

$^1$H NMR (CDCl$_3$) δ 1.22–1.36 (m, 24H), 1.54–1.68 (m, 4H), 3.36 (s, 3H), 3.51 (t, J=6.8 Hz, 2H), 3.67 (t, J=7.3 Hz, 2H), 4.62 (s, 2H), 7.69–7.71 (m, 2H), 7.83–7.85 (m, 2H)

PREPARATION EXAMPLE 24

16-Methoxymethoxyhexadecylamine

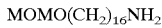

To a suspension of 0.97 g of N-(16-methoxymethoxyhexadecyl)phthalimide in 50 ml of ethanol was added 0.4 ml of hydrazine monohydrate and the mixture was heated under reflux for 2 hours. The reaction solution was distilled under reduced pressure. The residue was diluted with chloroform, washed with a 1N aqueous solution of sodium hydroxide, dried over anhydrous sodium sulfate and then distilled under reduced pressure. The residue was chromatographed over a silica gel column to afford the title compound as a colorless oily substance.

$^1$H NMR (CDCl$_3$) δ 1.23–1.46 (m, 26H), 1.55–1.62 (m, 2H), 2.68 (t, J=6.8 Hz, 2H), 3.36 (s, 3H), 3.51 (t, J=6.8 Hz, 2H), 4.62 (s, 2H)

PREPARATION EXAMPLE 25

16-Aminohexadecanol

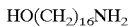

To a suspension of 0.65 g of 16-methoxymethoxyhexadecylamine in 40 ml of methanol was added 1 ml of conc. hydrochloric acid and the mixture was heated under reflux for one hour. The reaction solution was distilled under reduced pressure. The residue was diluted with a 1N aqueous solution of sodium hydroxide, extracted with chloroform, dried over anhydrous sodium sulfate and distilled under reduced pressure to afford the title compound as a colorless crystal.

$^1$H NMR (CDCl$_3$) δ 1.23–1.28 (m, 24H), 1.41–1.46 (m, 2H), 1.53–1.60 (m, 2H), 2.67 (t, J=6.8 Hz, 2H), 3.63 (t, J=6.3 Hz, 2H)

PREPARATION EXAMPLE 26

N-(16-Hydroxyhexadecyl)phthalimide

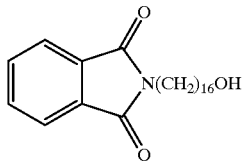

Synthesis was carried out in the same manner as described in Preparation Example 18 using as a starting material 1,16-hexadecanediol to afford the title compound.

$^1$H NMR (CDCl$_3$) δ 1.17–1.40 (m, 24H), 1.50–1.61 (m, 2H), 1.61–1.70 (m, 2H), 3.63 (t, J=6 Hz, 2H), 3.67 (t, J=7 Hz, 2H), 7.70 (dd, J=3, 5 Hz, 2H), 7.84 (dd, J=3, 5 Hz, 2H)

PREPARATION EXAMPLE 27

16-Aminohexadecanol

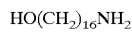

Synthesis was carried out in the same manner as described in Preparation Example 19 using as a starting material N-(16-hydroxyhexadecyl)phthalimide to afford the title compound.

PREPARATION EXAMPLE 28

Methyl 16-hydroxyhexadecanoate

Synthesis was carried out in the same manner as described in Preparation Example 20 from 16-hydroxyhexadecanoic acid and methanol to afford the title compound.

PREPARATION EXAMPLE 29

Methyl 16-phthalimidehexadecanoate

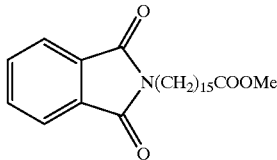

Synthesis was carried out in the same manner as described in Preparation Example 23 using as a starting material methyl 16-hydroxyhexadecanoate to afford the title compound.

$^1$H NMR (CDCl$_3$) δ 1.19–1.37 (m, 22H), 1.54–1.71 (m, 4H), 2.30 (t, J=8 Hz, 2H), 3.66 (s, 3H), 3.67 (t, J=7 Hz, 2H), 7.70 (dd, J=3 Hz, 5 Hz, 2H), 7.84 (dd, J=3 Hz, 5 Hz, 2H)

PREPARATION EXAMPLE 30

Methyl 16-aminohexadecanoate

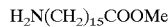

To a suspension of 3.08 g of methyl 16-phthalimidehexadecanoate in 100 ml of ethanol was added 3 ml of hydrazine monohydrate and the mixture was stirred overnight. The reaction solution was filtered, the filtrate was distilled. The residue thus obtained was extracted thrice with hot chloroform. The combined organic layer was distilled off to afford the title compound as a colorless crystal.

$^1$H NMR (CDCl$_3$) δ 1.20–1.36 (m, 22H), 1.43 (quint, J=7 Hz, 2H), 1.62 (quint, J=7 Hz, 2H), 2.30 (t, J=8 Hz, 2H), 2.67 (t, J=7 Hz, 2H), 3.67 (s, 3H)

PREPARATION EXAMPLE 31

16-Aminohexadecanol

In a mixed solvent of 75 ml of isopropyl ether and 25 ml of tetrahydrofuran was suspended 1.0 g of lithium aluminum hydride and to the suspension was added with stirring at room temperature 2.45 g of crystalline methyl 16-aminohexadecanoate and the mixture was stirred overnight. To the reaction solution were added successively 1 ml of water, 1 ml of a 10% aqueous solution of sodium hydroxide and 3 ml of water and the insolubles thus precipitated out were filtered off. The insolubles were extracted with a mixed solvent of chloroform and methanol. Then, the extract was combined with the filtrate and the mixture was distilled to afford the title compound as a colorless crystal.

PREPARATION EXAMPLE 32

16-Methoxymethoxyhexadecanal

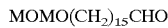

To a solution of 1.23 ml of oxalyl chloride in 60 ml of dichloromethane was added dropwise at −78 ° C. a solution of 2.0 ml of dimethyl sulfoxide in 2 ml of dichloromethane. After stirring for 10 minutes, a solution of 2.13 g of 16-methoxymethoxyhexadecanol in 30 ml of dichloromethane was added dropwise and the mixture was allowed to slowly rise up to −20° C. and then stirred for 15 minutes. 5.9 ml of triethylamine was added and the mixture was stirred at 0° C. for one hour. To the reaction solution was added a saturated aqueous solution of ammonium chloride and extracted with chloroform. The extract was dried over anhydrous sodium sulfate, distilled under reduced pressure and chromatographed over a silica gel column to afford the title compound as a colorless oily substance.

$^1$H NMR (CDCl$_3$) δ 1.22–1.29 (m, 22H), 1.37–1.66 (m, 4H), 2.42 (dt, J=1.9, 7.3 Hz, 2H), 3.36 (s, 3H), 3.51 (t, J=6.8 Hz, 2H), 4.62 (s, 2H), 9.76 (t, J=1.9 Hz, 1H)

PREPARATION EXAMPLE 33

Ethyl (E)-18-methoxymethoxy-2-octadecenoate

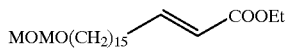

To a suspension of 0.31 g of sodium hydride in 50 ml of tetrahydrofuran was added dropwise at 0° C. a solution of 1.73 ml of diethyl phosphonacetic acid ethyl ester in 5 ml of tetrahydrofuran. After stirring for one hour, a solution of 2.17 g of 16-methoxymethoxyhexadecanal in 30 ml of tetrahydrofuran was added dropwise and then the mixture was stirred for 1.5 hours. To the reaction solution was added a saturated aqueous solution of ammonium chloride and extracted with ethyl acetate. The extract was washed with a saturated aqueous solution of sodium chloride, dried over anhydrous sodium sulfate and distilled off under reduced pressure. Chromatography over a silica gel afforded the title compound as a colorless oily substance.

$^1$H NMR (CDCl$_3$) δ 1.23–1.30 (m, 25H), 1.37–1.48 (m, 2H), 1.55–1.62 (m, 2H), 2.18 (dq, J=1.4, 7.3 Hz, 2H), 3.36 (s, 3H), 3.51 (t, J=6.3 Hz, 2H), 4.18 (q, J=7.3 Hz, 2H), 4.62 (s, 2H), 5.80 (dt, J=1.4,15.6 Hz, 1H), 6.96 (dt, J=6.8, 15.6 Hz, 1H)

PREPARATION EXAMPLE 34

Ethyl 18-methoxymethoxyoctadecanoate

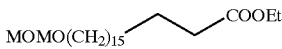

To a solution of 0.51 g of ethyl (E)-18-methoxymethoxy-2-octadecenoate in 30 ml of ethanol was added 0.06 g of 10% palladium carbon and the mixture was stirred overnight under hydrogen atmosphere. After filtering off the catalyst, the filtrate was distilled under reduced pressure to afford the title compound as a colorless oily substance.

$^1$H NMR (CDCl$_3$) δ 1.23–1.37 (m, 29H), 1.55–1.65 (m, 4H), 2.28 (t, J=7.3 Hz, 2H), 3.36 (s, 3H), 3.51 (t, J=6.8 Hz, 2H), 4.12 (q, J=7.8 Hz, 2H), 4.62 (s, 2H)

PREPARATION EXAMPLE 35

18-Methoxymethoxyoctadecanol

Synthesis was carried out in the same manner as described in Preparation Example 22 using as a starting material ethyl 18-methoxymethoxyoctadecanoate to afford the title compound as a colorless crystal.

$^1$H NMR (CDCl$_3$) δ 1.22–1.38 (m, 28H), 1.53–1.62 (m, 4H), 3.36 (s, 3H), 3.51 (t, J=6.8 Hz, 2H), 3.61–3.66 (m, 2H), 4.62 (s, 2H)

PREPARATION EXAMPLE 36

N-(18-Methoxymethoxyoctadecyl)phthalimide

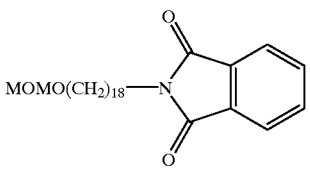

Synthesis was carried out in the same manner as described in Preparation Example 23 using as a starting material 18-methoxymethoxyoctadecanol to afford the title compound as a colorless crystal.

$^1$H NMR (CDCl$_3$) δ 1.22–1.36 (m, 28H), 1.55–1.70 (m, 4H), 3.36 (s, 3H), 3.51 (t, J=6.8 Hz, 2H), 3.67 (t, J=7.3 Hz, 2H), 4.62 (s, 2H), 7.69–7.71 (m, 2H), 7.83–7.85 (m, 2H)

PREPARATION EXAMPLE 37

18-Methoxymethoxyoctadecylamine

Synthesis was carried out in the same manner as described in Preparation Example 24 using as a starting material N-(18-methoxymethoxyoctadecyl)phthalimide to afford the title compound as a colorless waxy substance.

$^1$H NMR (CDCl$_3$) δ 1.22–1.35 (m, 28H), 1.37–1.47 (m, 2H), 1.55–1.62 (m, 2H), 2.68 (t, J=6.8 Hz, 2H), 3.36 (s, 3H), 3.51 (t, J=6.8 Hz, 2H), 4.62 (s, 2H)

PREPARATION EXAMPLE 38

18-Aminooctadecanol

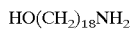

Synthesis was carried out in the same manner as described in Preparation Example 25 using as a starting material 18-methoxymethoxyoctadecylamine to afford the title compound as a colorless crystal.

$^1$H NMR (CDCl$_3$) δ 1.24–1.46 (m, 30H), 1.56 (quint, J=6.8 Hz, 2H), 2.67 (t, J=6.8 Hz, 2H), 3.63 (t, J=6.8 Hz, 2H)

PREPARATION EXAMPLE 39

Dimethyl 1,18-octadecanedioate

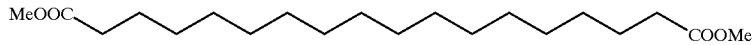

To a suspension of 10.18 g of 1,18-octadecanedioic acid in 200 ml of methanol was added dropwise at room temperature with stirring 1 ml of thionyl chloride and the mixture was stirred for 50 minutes. The reaction solution was stirred at 60° C. for a further one hour and then allowed to cool. The crystal thus precipitated out was recovered by filtration to afford 10.78 g of the title compound.

$^1$H NMR (CDCl$_3$) δ 1.17–1.37 (m, 24H), 1.62 (quint, J=7 Hz, 4H), 2.30 (t, J=8 Hz, 4H), 3.67 (s, 6H)

PREPARATION EXAMPLE 40

1,18-Octadecanediol

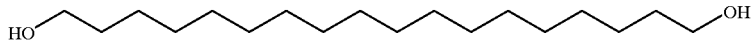

Synthesis was carried out in the same manner as described in Preparation Example 16 using as a starting material dimethyl 1,18-octadecanedioate to afford the title compound as a colorless crystal.

$^1$H NMR (CDCl$_3$) δ 1.16–1.40 (m, 28H), 1.57 (quint, J=7 Hz, 4H), 3.64 (t, J=7 Hz, 4H)

PREPARATION EXAMPLE 41

N-(18-Hydroxyoctadecyl)phthalimide

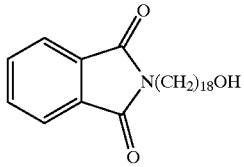

Synthesis was carried out in the same manner as described in Preparation Example 17 using as a starting material 1,18-octadecanediol to afford the title compound as a crystal.

$^1$H NMR (CDCl$_3$) δ 1.16–1.41 (m, 28H), 1.50–1.62 (m, 2H), 1.67 (quint, J=7 Hz, 2H), 3.64 (q, J=6 Hz, 2H), 3.67 (t, J=7 Hz, 2H), 7.70(dd, J=3 Hz, 5 Hz, 2H), 7.84 (dd, J=3 Hz, 5 Hz, 2H)

PREPARATION EXAMPLE 42

18-Aminooctadecanol

Synthesis was carried out in the same manner as described in Preparation Example 19 using as a starting material N-(18-hydroxyoctadecyl)phthalimide to afford the title compound as a crystal.

$^1$H NMR (CDCl$_3$) δ 1.18–1.39 (m, 28H), 1.43 (quint, J=7 Hz, 2H), 1.56 (quint, J=7 Hz, 2H), 2.68 (q, J=7 Hz, 2H), 3.64 (t, J=7 Hz, 2H)

PREPARATION EXAMPLE 43

1-Isopropylpiperazine

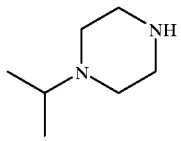

PREPARATION EXAMPLE 43-1

1-Acetyl-4-isopropylpiperazine

To a mixture of 12.95 g of piperazine, 0.75 g of sodium iodide and 3.46 g of potassium carbonate were added successively 25 ml of methanol and 6.15 g of 2-bromopropane and the mixture was stirred at 60° C. for 4 hours. Chloroform was added, washed with a saturated aqueous solution of sodium chloride, and dried over anhydrous magnesium sulfate. The solvent was distilled off under reduced pressure, 12 ml of acetic anhydride was added gradually and the mixture was stirred at room temperature for 2.5 hours. The reaction solution was poured into ice, chloroform was added and then it was neutralized with sodium carbonate. After extracted with chloroform, the extract was dried over anhydrous magnesium sulfate and the solvent was distilled off under reduced pressure. The residue thus obtained was chromatographed over a silica gel column and the solvent was distilled off. The residue thus precipitated out was allowed to stand overnight and the diacetylpiperazine was filtered off to afford 7.26 g of the title compound as an oily substance.

$^1$H NMR (CDCl$_3$) δ 1.04 (d, J=6 Hz, 6H), 2.08 (s, 3H), 2.47 (t, J=5 Hz, 2H), 2.51 (t, J=5 Hz, 2H), 2.71 (sept, J=6 Hz, 1H), 3.46 (t, J=5 Hz, 2H), 3.62 (t, J=5 Hz, 2H)

PREPARATION EXAMPLE 43-2

1-Isopropylpiperazine

A mixture of 7.26 g of 1-acetyl-4-isopropylpiperazine, 100 ml of methanol and 10 g of potassium hydroxide was heated under reflux for 17 hours. After the solvent was distilled off, water and chloroform were added to perform extraction with chloroform and the extract was dried over anhydrous magnesium sulfate. The solvent was distilled off under reduced pressure to afford 5.78 g of the title compound as an oily substance.

$^1$H NMR (CDCl$_3$) δ 1.05 (d, J=6 Hz, 6H), 2.49 (bt, J=5 Hz, 4H), 2.75 (sept, J=6 Hz, 1H), 2.90 (t, J=5 Hz, 4H)

PREPARATION EXAMPLE 44

Sodium 6-(4-methyl-1-piperazinyl)pyridine-3-carboxylate

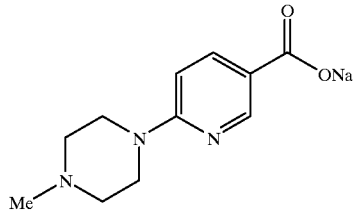

To a solution of 1.48 g of sodium hydroxide in 4 ml of water were added 40 ml of methanol and 8.70 g of methyl 6-(4-methyl-1-piperazinyl)pyridine-3-carboxylate and the mixture was heated under reflux for 2 hours. Then, 0.20 g of sodium hydroxide was added and the mixture was heated under reflux for a further one hour and the solvent was distilled off. The residue was dispersed in acetone, recovered by filtration and dried under reduced pressure to afford the title compound as a crystal. This product was used for the subsequent reaction without purification.

PREPARATION EXAMPLE 45

Methyl 6-(4-methyl-1-piperazinyl)pyridine-3-carboxylate

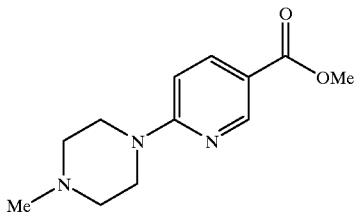

To 10.2 g of methyl 6-chloronicotinate were added 6.24 g of methylpiperazine, 6 g of diisopropylamine, 6.1 g of sodium iodide and 60 ml of DMF and the mixture was stirred at 120° C. for 4 hours. After water was added, the reaction solution was extracted with ethyl acetate and the extract was washed with a saturated aqueous solution of sodium chloride and then distilled under reduced pressure to afford the title compound as a crystal.

Pharmacological test results of the pyridinecarboxamide derivatives (I) of the present invention will be shown below.

For comparison, the compound of Example 10 and the compound of Example 2 of JP-A-5-32630 were used, namely, N-(11-nitroxy-1-undecanyl)-6-(4-methyl-1-piperazinyl)nicotinamide (hereinafter referred to as "Comparative Compound 1"), and N-(12-nitroxy-1-dodecanyl)-6-(4-methyl-1-piperazinyl)nicotinamide (hereinafter referred to as "Comparative Compound 2").

The compounds of the present invention will be shown below in terms of the corresponding Example numbers. For example, "Compound 1" is meant to indicate the compound obtained by the present Example 1.

1. Behavior suppressing action

The effect of the present pyridinecarboxamide derivatives on general behaviors of mice was studied.

Using ddY-strain mice of 7 weeks old, test substance was administered at 100μl 1/10 sec to the tail vein and behavior of the animal was observed over one hour. After the administration, sedative animal was evaluated as sedated, while animal with behavioral suppression was evaluated as suppressed.

TABLE 1

| Test substance | R | n | Behavioral suppression (10 mg/kg) |
| --- | --- | --- | --- |
| Compound 1 | Me | 14 | Non |
| Compound 5 | Et | 14 | Non |
| Compound 6 | H | 14 | Non |
| Compound 7 | n-Pr | 14 | Non |
| Compound 8 | i-Pr | 14 | Non |
| Compound 9 | Me | 16 | Non |
| Compound 10 | Et | 16 | Non |
| Compound 11 | i-Pr | 16 | Non |
| Compound 13 | Me | 18 | Non |
| Comparative Compound 1 | Me | 11 | Sedated |

No abnormalities were observed in general behaviors with Compounds 1, 5, 6, 7, 8, 9, 10, 11 and 13. However, it has become apparent that Comparative Compound 1 is not desirable as a therapeutic agent for cerebrovascular disorders because of the suppression of behavior being shown.

2. Cerebral protective action

Cerebral protective action of the pyridinecarboxamide derivatives of this invention (an anti-anoxia action) were studied using a hypoxic model of mice.

Using ddY-strain male mice of 6 weeks old, the test substance of Compound 1, Compound 10 or Compound 11 was intravenously administered to the tail vein at the dose of 1.0 mg/kg. After 30 minutes from the administration, animals were decapitated to measure a gasping duration. This measurement was made by two persons who had not been informed of the test substances and the measured values were averaged to obtain the data. Also, the test was carried out in the same manner as described above except that Comparative Compound 1 was administered instead of the test substances.

The action of each substance will be shown in Table 2, with the gasping time of Comparative Compound 1 being defined as 1.

TABLE 2

| Test substance | R | n | Gasping duration |
| --- | --- | --- | --- |
| Compound 1 | Me | 14 | 2.6 |
| Compound 10 | Et | 16 | 1.7 |
| Compound 11 | i-Pr | 16 | 1.4 |
| Comparative Compound 1 | Me | 11 | 1 |

The pyridinecarboxamide derivatives of this invention had a 1.4 to 2.6 times higher cerebral protective action than Comparative Compound 1.

It is believed that grasping after decapitation is controlled by the respiratory center and, if the nervous functions are maintained by the respiratory center, the gasping duration would be prolonged. Moreover, it is suggested that the ischemia with decapitation is related to the decrease in the intracerebral glucose which is believed to be essential as a nutrition component in the brain. In view of the foregoing, the pyridinecarboxamide derivatives of this invention can prolong the gasping duration and then are useful as a cerebral protective agent.

3. Anti-cerebral edema action (Obstructive cerebral ischemia model using polyvinyl acetate)

Inhibiting action on cerebral ischemia was studied in an obstructive cerebral ischemia model using polyvinyl acetate.

The obstructive model was prepared as described below. (Hiroyoshi Nishi et al., Stroke 1989, 20:1236–1240)

Wistar-strain male rats weighing 200–350 g were used and fixed at the dorsal position under anesthesia of ether and then the left common carotid artery, internal carotid artery, external carotid artery were isolated. The external carotid artery was ligated, the pterylgopalatine artery was fastened with clamp and a cannula was inserted from the external carotid artery toward the branch between the internal carotid artery and the common carotid artery. 5 μl of a 3% polyvinyl acetate/52% ethanol solution in water was injected. After 30 seconds, the clamp was removed from the artery and then the wound was sutured. After 24 hours, animal was decapitated and the cerebrum was isolated, within 120 seconds from which wet weights of the left cerebrum and the right cerebrum were measured. The left and right cerebra were dried in an oven at 105° C. for 24 hours and then the dry weights were measured. A cerebral water content was calculated according to the following equation:

$$\text{Cerebral water content}(\%) = \{(\text{Wet weight} - \text{Dry weight})/\text{Wet weight}\} \times 100$$

Compound 1 or Compound 9 was intravenously injected to the tail vein at the doses of 1.0 mg/kg and 3.0 mg/kg before 5 minutes from the administration of polyvinyl acetate.

Inhibitory rate of cerebral edema in the cerebral edema model using polyvinyl acetate are shown in Table 3.

TABLE 3

| Test substance | R | n | 1 mg/kg |
| --- | --- | --- | --- |
| Compound 1 | Me | 14 | 44.0% |
| Compound 9 | Me | 16 | 33.3% |

Compounds 1 and 9 inhibited cerebral edema at 44.0% and 33.3%, respectively.

4. Anti-cerebral edema action (Ischemic reperfusion model using SHR-SP)

The pyridinecarboxamide derivatives of this invention were studied for the inhibitory action on cerebral edema with the model using SHR-SP (Spontaneous hypertensive rats which are vulnerable to cerebral hemorrhage).

Male SHR-SP of 15–17 weeks old were measured for the blood pressure one day before the testing and classified into groups. Both common carotid arteries were separated under pentobarbital anesthesia at 35 mg/kg and common carotid arteries were fastened by clamp to cause ischemia. After 2 hours, the clamp was removed from the common carotid artery to reperfuse. After a further 2 hours, the animal was decapitated and the cerebrum excised under ether anesthesia. The cerebrum was dried in an oven at 105° C. for 24 hours and the cerebral water content (%) was calculated.

$$\text{Cerebral water content}(\%) = (\text{Wet weight} - \text{Dry weight})/\text{Wet weight} \times 100$$

Compound 1 and Comparative Compound 2 were intravenously administered twice, that is, immediately after the ischemia and immediately before the reperfusion at the dose of 1 mg/kg, respectively.

Inhibitory rates of cerebral ischemia by Compound 1 and Comparative Compound 2 are shown in Table 3-2.

TABLE 3-2

| Test substance | R | n | |
| --- | --- | --- | --- |
| Compound 1 | Me | 14 | 63% |
| Comparative Compound 2 | Me | 12 | −90% |

Compound 1 showed a potent anti-cerebral edema activity, whereas Comparative Compound 2 made cerebral edema worse.

5. Inhibitory rate of delayed neuronal death

MON/Jms/Gbs-strain male jirds (weighing 60–80 g) were fixed at the dorsal position under 1.5–2.0% halothane anesthesia and the common carotid artery was isolated. Ischemia was caused by fastening the common carotid artery with clamp for 3 minutes and then reperfused. After 7 days, the brain was excised under ether anesthesia and fixed with 10% formalin for 2 days and then tissue slices of the hippocampus were prepared. The hippocampus CA1 cells were stained using HE staining and the survival rate of the CA1 cells was evaluated.

Compound 1 was administered to the carotid artery at the dose of 0.5 mg/kg immediately after ischemia. Using as a control the case wherein the drug was not administered, inhibitory rate was calculated according to the following equation:

Inhibitory rate = (1 − (survival rate of Compound 1 administered $CA1$ / Survival rate of control $CA1$ cells) × 100(%)

TABLE 4

| | R | n | Inhibitory rate |
|---|---|---|---|
| Compound 1 | Me | 14 | 47% |

6. Hypotensive activity

The action on blood pressure was studied using rats.

Using Wistar-strain male rats, animals were anesthetized by intraperitoneal administration of thiopental and then a tracheal cannula, a cannula for measuring blood pressure into the right femoral artery, a cannula for continuous anesthesia into the right femoral vein and a cannula for administering Compound 1, Compound 5, Compound 8 and Compound 9 into the left femoral vein were inserted. In the right femoral artery cannula, blood pressure was measured by means of an amplifier for measuring blood pressure (Nihon Koden Co., Ltd., AP-601G) via a transducer (Gould, CA930). α-Chloralose was administered at 40 mg/kg/hr via the right femoral vein cannula to maintain anesthesia. The tracheal cannula was connected to a respirator (Haward, MODEL 683) and controlled respiration was applied at 50 strokes/min., 1 ml/100 g b.w. And, 100% oxygen was charged to the inspiratory port of the respirator and an oxygen rate was adjusted to 50 ml/min. by means of a flow meter. A rectum temperature was maintained at 37° C. by means of a heating pad.

After blood pressure was stabilized, test substance was administered at 1.0 mg/kg via the vein cannula. Also, Comparative Compound 2 was administered as a control substance in the same manner as described above. The blood pressure was measured after one minute from the administration of the test substance and a percent to the blood pressure value before the administration was calculated.

TABLE 5

| Test substance | R | n | Decrease in blood pressure (%) |
|---|---|---|---|
| Compound 1 | Me | 14 | 11.2 |
| Compound 5 | Et | 14 | 15.2 |
| Compound 8 | i-Pr | 14 | 10.2 |
| Compound 9 | Me | 16 | 7.7 |
| Comparative Compound 2 | Me | 12 | 43.9 |

It is shown from Table 5 that the pyridinecarboxamide derivatives of this invention do hardly affect blood pressure. However, it is believed that the compound of Comparative Compound 2 could make worse the ischemic condition derived from cerebrovascular disorders and then is not desirable as a therapeutic agent for cerebral edema in view of the decrease of the blood pressure of 44%.

7. Inhibitory action on lipid peroxidation

Inhibitory action on lipid peroxidation was studied in rat brain homogenate.

Wistar-strain male rats (weighing 230–300 g) were decapitated and the cerebrum was quickly excised. A 4 times volume of a solution of 50 mM phosphoric acid and 0.142 mM NaCl (pH 7.4) was added and the mixture was homogenated and then centrifuged at 3000 rpm for 10 minutes. The supernatant thus obtained was prepared to give a protein level of 2 mg/ml.

Determination of lipid peroxide was carried out using TBA method (thiobarbituric acid). To the brain homogenate was added each of Compound 1, Compound 5, Compound 6, Compound 8, Compound 9, Compound 11 and Compound 14 as a test substance to give a final concentration of $10^{-4}$M, thereby initiating the reaction. After incubation at 37° C. for 15 minutes, the reaction was stopped in ice by adding a 35% perchloric acid solution. The reaction mixture was centrifuged at 4° C. and 1000 rpm for 5 minutes and to the supernatant thus obtained was added a 0.5% TBA solution. The mixture was boiled at 100° C. for 15 minutes. After cooling, absorbance was determined at 532 nm. 1,1,3,3-Tetraethoxypropane as a standard was subjected to the reaction in the same manner as above and an amount of lipid peroxide, that is, an amount of the malondialdehyde (MDA) produced was determined from the absorbance.

Inhibitory rate of lipid peroxidation was calculated according to the following equation:

Inhibitory rate of lipid peroxidation = [1 − {MDA nmol(test substance; incubated for 15 min.) − MDA nmol (test substance; incubated for 0 min.)}/{MDA nmol (solvent; incubated for 15 min.) − MDA nmol (solvent; incubated for 0 min.)}] × 100(%)

TABLE 6

| Test substance | R | n | Inhibitory rate of lipid peroxidation (%) |
|---|---|---|---|
| Compound 1 | Me | 14 | 91 |
| Compound 5 | Et | 14 | 69 |
| Compound 6 | H | 14 | 59 |
| Compound 8 | i-Pr | 14 | 70 |
| Compound 9 | Me | 16 | 72 |
| Compound 11 | i-Pr | 16 | 53 |
| Compound 14 | H | 18 | 75 |

It was observed from the results of Table 6 that the pyridinecarboxamide derivatives of this invention have an inhibitory action on lipid peroxidation.

We claim:
1. A pyridinecarboxamide derivative of the formula (1)

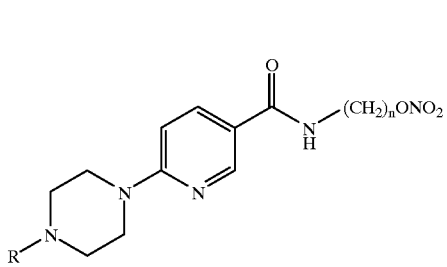

(1)

(wherein n represents an integer of 14–18, and R represents a hydrogen atom or a straight or branched $C_1$–$C_4$ alkyl group) or a physiologically acceptable salt thereof.

2. The pyridinecarboxamide derivative as claimed in claim 1 wherein n is 14, 16 or 18 in the said formula (1).

3. The pyridinecarboxamide derivative as claimed in claim 1 or 2 wherein R is a hydrogen atom, a methyl group, an ethyl group or an isopropyl group.

4. The pyridinecarboxamide derivative as claimed in claim 1 wherein it is N-(14-nitroxytetradecyl)-6-(4-methyl-1-piperazinyl)pyridine-3-carboxamide or a physiologically acceptable salt thereof.

5. The pyridinecarboxamide derivative as claimed in claim 1 wherein it is N-(16-nitroxyhexadecyl)-6-(4-methyl-1-piperazinyl)pyridine-3-carboxamide or a physiologically acceptable salt thereof.

6. A compound of the formula (2)

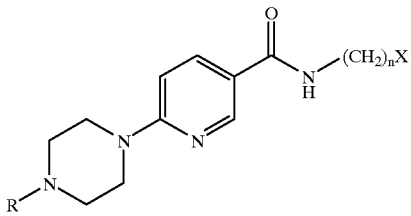

(2)

(wherein n represents an integer of 14–18, R represents a hydrogen atom or a straight or branched $C_1$–$C_4$ alkyl group and X represents a hydroxyl group, a mesyloxy group, a tosyloxy group, a bromine atom or an iodine atom).

7. A process for the preparation of a pyridinecarboxamide derivative represented by the formula (I)

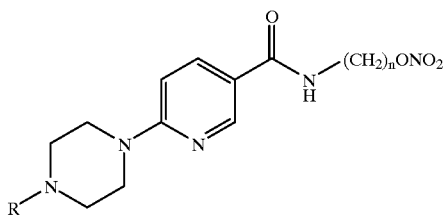

(1)

wherein n represents an integer of 14–18, and R represents a hydrogen atom or a straight or branched chain $C_1$–$C_4$ alkyl group, which comprises reacting an alkali metal salt, halide or acid anhydride of a 6-piperazinylpyridine-3-carboxylic acid of the formula (3):

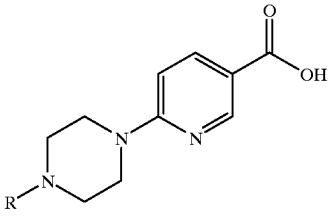

(3)

wherein R represents a hydrogen atom or a straight or branched $C_1$–$C_4$ alkyl group, with a ω-aminoalkyl nitrate represented by the formula (4):

$H_2N(CH_2)_nONO_2$ (4)

wherein n represents an integer of 14–18, or an acid addition salt thereof.

8. A process for the preparation of a pyridinecarboxamide derivative represented by the formula (1)

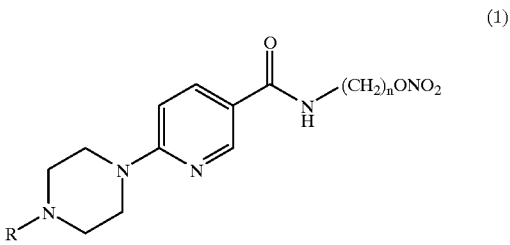

(1)

wherein n represents an integer of 14–18, and R represents a hydrogen atom or a straight or branched chain $C_1$–$C_4$ alkyl group, which comprises reacting a compound represented by the said formula (2)

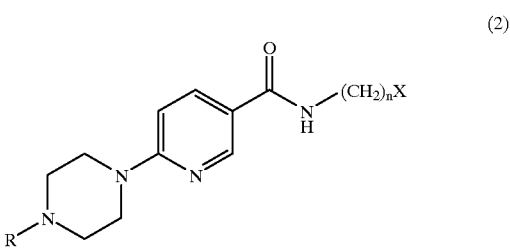

(2)

wherein n represents an integer of 14–18, and R represents a hydrogen atom or a straight or branched chain $C_1$–$C_4$ alkyl group, and X represents a hydroxyl group, a mesyloxy group, a tosyloxy group, a bromine atom or an iodine atom, with a nitrating agent.

9. A pharmaceutical composition which comprises a pyridinecarboxamide derivative of formula (1)

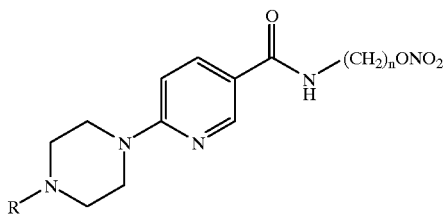

(1)

wherein n represents an integer of 14–18, and R represents a hydrogen atom or a straight or branched chain $C_1$–$C_4$ alkyl group, or a physiologically acceptable salt thereof, and a pharmaceutically acceptable excipient.

10. The pharmaceutical composition of claim 9, wherein the pyridinecarboxamide derivative of the formula (1) or a physiologically acceptable salt thereof, is present in a cerebral edema treating effective amount.

11. A method for treatment of cerebral edema which comprises administering to patients suffering from cerebral edema an effective amount of a pyridinecarboxamide derivative of the formula (1)

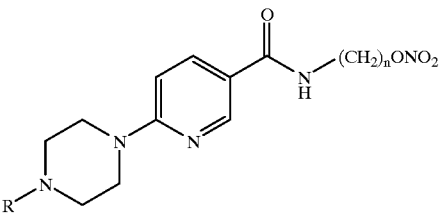

(1)

wherein n represents an integer of 14–18, and R represents a hydrogen atom or a straight or branched chain $C_1$–$C_4$ alkyl group, or a physiologically acceptable salt thereof.

* * * * *